(12) United States Patent
Berkely

(10) Patent No.: US 11,464,611 B2
(45) Date of Patent: Oct. 11, 2022

(54) ADAPTERS WITH LIGHT SOURCES FOR DENTAL AIR/WATER SYRINGES

(71) Applicant: Donovan Berkely, Irvine, CA (US)

(72) Inventor: Donovan Berkely, Irvine, CA (US)

( * ) Notice: Subject to any disclaimer, the term of this patent is extended or adjusted under 35 U.S.C. 154(b) by 863 days.

(21) Appl. No.: 16/158,459

(22) Filed: Oct. 12, 2018

(65) Prior Publication Data

US 2019/0105140 A1  Apr. 11, 2019

Related U.S. Application Data

(63) Continuation of application No. 14/530,380, filed on Oct. 31, 2014, now abandoned, which is a continuation-in-part of application No. 13/907,296, filed on May 31, 2013, now abandoned, which is a continuation-in-part of application No. 13/841,280, filed on Mar. 15, 2013, now abandoned.

(60) Provisional application No. 61/898,605, filed on Nov. 1, 2013, provisional application No. 61/619,578, filed on Apr. 3, 2012.

(51) Int. Cl.
*A61C 17/02* (2006.01)
*A61C 1/08* (2006.01)
*A61B 1/247* (2006.01)

(52) U.S. Cl.
CPC .......... *A61C 17/0217* (2013.01); *A61B 1/247* (2013.01); *A61C 1/088* (2013.01); *A61C 17/0202* (2013.01)

(58) Field of Classification Search
CPC . A61C 17/0202; A61C 17/0217; A61C 17/02; A61C 19/063; A61C 1/0076; A61B 1/0684

USPC ........................................................... 433/80
See application file for complete search history.

(56) References Cited

U.S. PATENT DOCUMENTS

| 1,858,056 | A |   | 5/1932  | Pieper         |             |
|-----------|---|---|---------|----------------|-------------|
| 3,254,646 | A |   | 6/1966  | Staunt et al.  |             |
| 3,401,691 | A | * | 9/1968  | Beu ..................... | A61C 17/0217 |
|           |   |   |         |                | 137/625.33  |
| 3,698,088 | A | * | 10/1972 | Austin, Jr. ......... | A61C 17/0217 |
|           |   |   |         |                | 433/80      |
| 3,874,083 | A |   | 4/1975  | Buckley        |             |

(Continued)

FOREIGN PATENT DOCUMENTS

WO    2000/33762    6/2000

*Primary Examiner* — Edward Moran
*Assistant Examiner* — Matthew P Saunders
(74) *Attorney, Agent, or Firm* — Dinsmore & Shohl LLP

(57) ABSTRACT

A method of converting an air/water dental syringe of the type having a syringe body and an autoclavable dental tip and lacking illumination into a converted air/water dental syringe adapted to be used with a disposable dental tip different from the autoclavable dental tip and with illumination capabilities includes using a conversion kit having a retainer body and a self-contained module. The syringe body is attached to a proximal end of the retainer body through a proximal opening for providing air and water. A proximal end is inserted into a distal opening of the retainer body. The self-contained module includes a light-emitting diode (LED), a battery powering the LED, and a switch to turn the LED ON and OFF. Light emitted from the LED provides illumination through a light opening on an outer surface of the retainer body generally towards a distal end of the disposable dental tip.

12 Claims, 23 Drawing Sheets

(56) References Cited

U.S. PATENT DOCUMENTS

| | | | |
|---|---|---|---|
| 4,026,025 A * | 5/1977 | Hunt | A61C 17/0217 433/80 |
| 4,248,589 A * | 2/1981 | Lewis | A61C 17/0217 433/80 |
| 4,515,564 A | 5/1985 | Lohn | |
| 4,552,131 A * | 11/1985 | Omagari | G02B 23/2453 600/165 |
| 4,629,425 A * | 12/1986 | Detsch | A61B 1/253 433/29 |
| 4,810,194 A | 3/1989 | Snedden | |
| 5,049,071 A * | 9/1991 | Davis | A61C 17/0202 222/145.5 |
| 5,192,206 A * | 3/1993 | Davis | A61C 17/0202 433/80 |
| 5,236,356 A * | 8/1993 | Davis | A61C 17/0202 433/80 |
| 5,242,300 A | 9/1993 | Esrock | |
| 5,286,065 A * | 2/1994 | Austin | A61C 17/0202 285/23 |
| 5,306,146 A * | 4/1994 | Davis | A61C 17/0202 433/80 |
| 5,336,202 A | 8/1994 | Bailly et al. | |
| 5,342,195 A * | 8/1994 | Davis | A61C 17/0202 433/80 |
| D352,354 S | 11/1994 | Davis et al. | |
| 5,433,485 A * | 7/1995 | Austin, Jr. | A61C 17/0202 285/23 |
| 5,460,619 A * | 10/1995 | Esrock | A61C 17/0217 433/80 |
| 5,489,205 A * | 2/1996 | Davis | A61C 17/0202 433/80 |
| 5,554,025 A | 9/1996 | Kinsel | |
| 5,591,389 A | 1/1997 | Esrock | |
| 5,616,028 A | 4/1997 | Hafele et al. | |
| 5,643,175 A * | 7/1997 | Adair | A61B 1/00142 600/156 |
| 5,772,433 A * | 6/1998 | Esrock | A61C 17/0217 433/80 |
| 5,833,456 A * | 11/1998 | Davis | A61C 1/088 433/29 |
| 5,848,893 A | 12/1998 | Martin et al. | |
| 5,882,194 A | 3/1999 | Davis et al. | |
| 5,882,197 A | 3/1999 | Davis et al. | |
| 5,899,692 A * | 5/1999 | Davis | A61C 17/02 433/29 |
| 5,908,296 A | 6/1999 | Kipke et al. | |
| 5,927,975 A * | 7/1999 | Esrock | A61C 1/18 285/133.11 |
| 5,947,729 A * | 9/1999 | Bell | A61C 1/0015 433/98 |
| 5,961,326 A | 10/1999 | Johnston et al. | |
| 6,048,200 A * | 4/2000 | Martin | A61C 17/0202 433/80 |
| 6,079,979 A | 6/2000 | Riitano | |
| 6,093,020 A | 7/2000 | Pond et al. | |
| 6,095,810 A * | 8/2000 | Bianchetti | A61C 1/088 433/29 |
| 6,113,391 A | 9/2000 | Esrock | |
| 6,149,429 A * | 11/2000 | Bukowski | A61C 17/0202 433/80 |
| 6,238,211 B1 * | 5/2001 | Esrock | A61C 17/0202 433/80 |
| 6,250,921 B1 * | 6/2001 | Esrock | A61C 17/0202 433/80 |
| RE37,324 E | 8/2001 | Esrock | |
| 6,283,750 B1 | 9/2001 | Esrock | |
| 6,319,001 B1 | 11/2001 | Esrock | |
| 6,322,361 B1 | 11/2001 | Esrock | |
| 6,390,815 B1 | 5/2002 | Pond | |
| 6,419,485 B1 | 7/2002 | Pond | |
| 6,464,498 B1 | 10/2002 | Pond | |
| 6,500,000 B1 * | 12/2002 | Segal | A61C 17/0202 433/80 |
| 6,510,970 B2 * | 1/2003 | McLean | A61C 17/0202 433/80 |
| 6,533,578 B2 | 3/2003 | Segal | |
| 6,926,502 B2 | 8/2005 | Lin et al. | |
| 7,104,794 B2 * | 9/2006 | Levy | A61C 1/07 433/119 |
| 7,431,587 B2 | 10/2008 | Pond | |
| 7,993,135 B2 | 8/2011 | Nesbitt et al. | |
| 8,162,906 B2 * | 4/2012 | Terrill | A61D 7/00 604/311 |
| 8,926,502 B2 * | 1/2015 | Levy | A61B 1/126 600/129 |
| 9,101,266 B2 * | 8/2015 | Levi | A61B 1/00181 |
| 9,173,726 B2 * | 11/2015 | Sabourin | A61C 1/088 |
| 9,295,377 B2 * | 3/2016 | Oneda | A61B 1/00029 |
| 9,655,502 B2 * | 5/2017 | Levy | A61B 1/00114 |
| 9,795,289 B2 * | 10/2017 | Clayton | A61B 1/24 |
| 9,993,142 B2 | 6/2018 | Salman et al. | |
| 10,045,685 B2 * | 8/2018 | Bayer | A61B 1/00177 |
| 2001/0041321 A1 | 11/2001 | Segal | |
| 2004/0224281 A1 * | 11/2004 | Bain | A61C 17/0202 433/80 |
| 2005/0032017 A1 * | 2/2005 | Levy | A61C 1/088 433/119 |
| 2005/0182299 A1 * | 8/2005 | D'Amelio | G02B 23/2423 600/172 |
| 2006/0063976 A1 | 3/2006 | Aizenfeld et al. | |
| 2006/0124862 A1 * | 6/2006 | Rodriquez | A61B 90/35 250/462.1 |
| 2006/0161117 A1 * | 7/2006 | Young | A61M 25/0097 600/178 |
| 2006/0234185 A1 * | 10/2006 | Ziemba | A61C 3/03 433/119 |
| 2007/0106119 A1 | 5/2007 | Hirata et al. | |
| 2007/0142711 A1 * | 6/2007 | Bayer | A61B 1/00101 600/172 |
| 2008/0002402 A1 * | 1/2008 | Mandikos | A61C 19/003 433/29 |
| 2008/0096161 A1 * | 4/2008 | Cain | A61C 17/0217 433/80 |
| 2009/0202961 A1 * | 8/2009 | Fani | A61C 17/20 433/119 |
| 2010/0273123 A1 * | 10/2010 | Mecher | A61C 19/004 433/29 |
| 2010/0286659 A1 | 11/2010 | Terrill et al. | |
| 2010/0298640 A1 * | 11/2010 | Oneda | A61B 1/00105 600/109 |
| 2011/0143304 A1 | 6/2011 | Jamnia et al. | |
| 2011/0275026 A1 | 11/2011 | Smith | |
| 2012/0253121 A1 | 10/2012 | Kitano | |
| 2013/0109916 A1 * | 5/2013 | Levy | A61B 1/00177 600/109 |
| 2013/0172670 A1 * | 7/2013 | Levy | A61B 1/00181 600/110 |
| 2013/0203014 A1 * | 8/2013 | Lieb | A61C 1/12 433/29 |
| 2013/0260333 A1 * | 10/2013 | Berkely | A61C 17/0217 433/80 |
| 2014/0329198 A1 * | 11/2014 | Esrock | A61C 17/0202 433/89 |
| 2014/0349244 A1 * | 11/2014 | Patel | A61M 5/427 433/29 |
| 2014/0356803 A1 * | 12/2014 | Clayton | A61B 1/247 433/29 |
| 2015/0024335 A1 * | 1/2015 | Sabourin | A61C 17/0202 433/27 |
| 2015/0050613 A1 * | 2/2015 | Berkely | A61C 17/022 433/29 |
| 2015/0182320 A1 * | 7/2015 | Berkely | A61M 5/3286 433/89 |
| 2015/0209124 A1 * | 7/2015 | Berkely | A61C 17/0202 433/29 |
| 2016/0135935 A1 * | 5/2016 | Chen | A61C 17/022 433/32 |
| 2016/0310247 A1 * | 10/2016 | Wang | A61C 17/0217 |

* cited by examiner

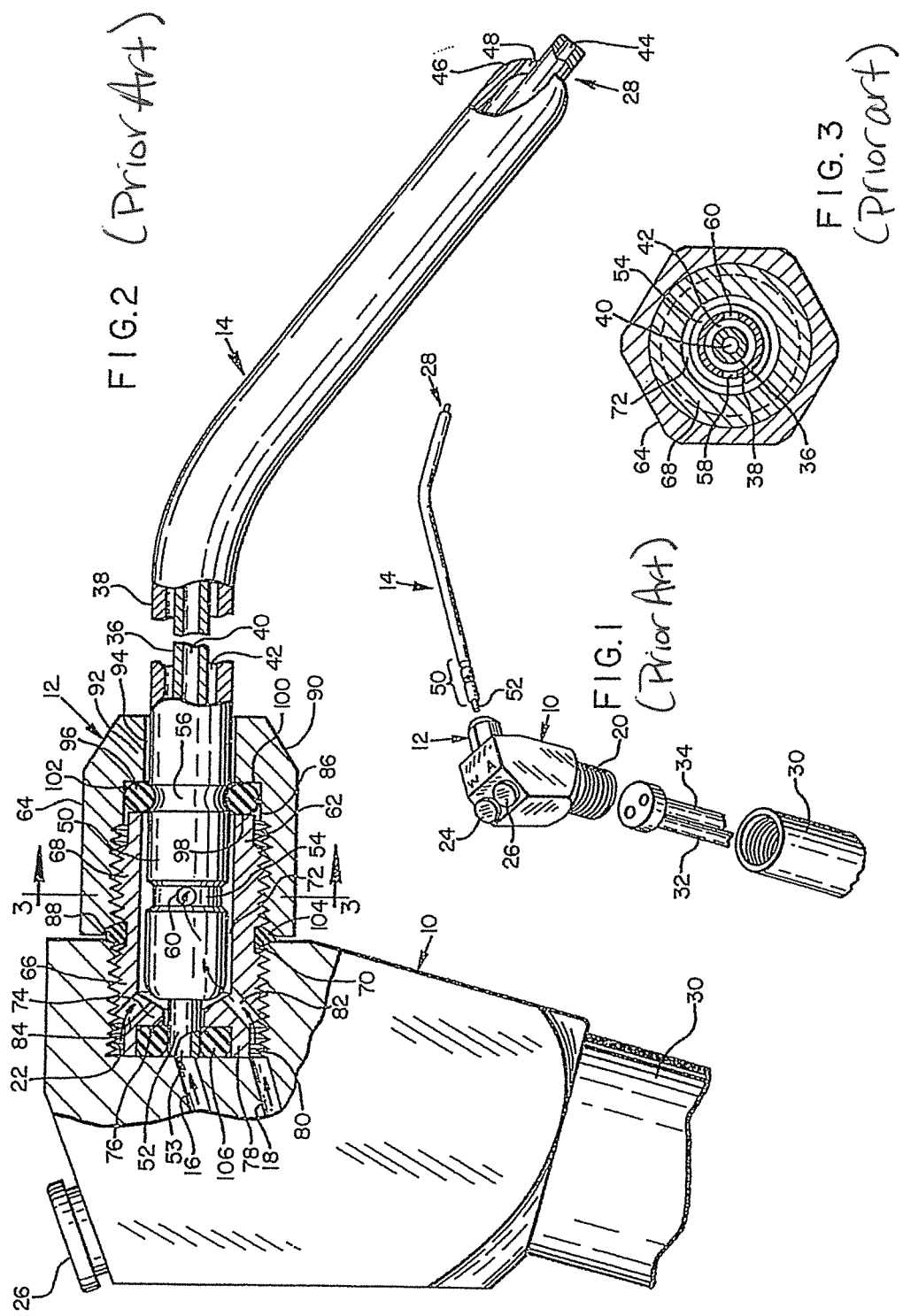

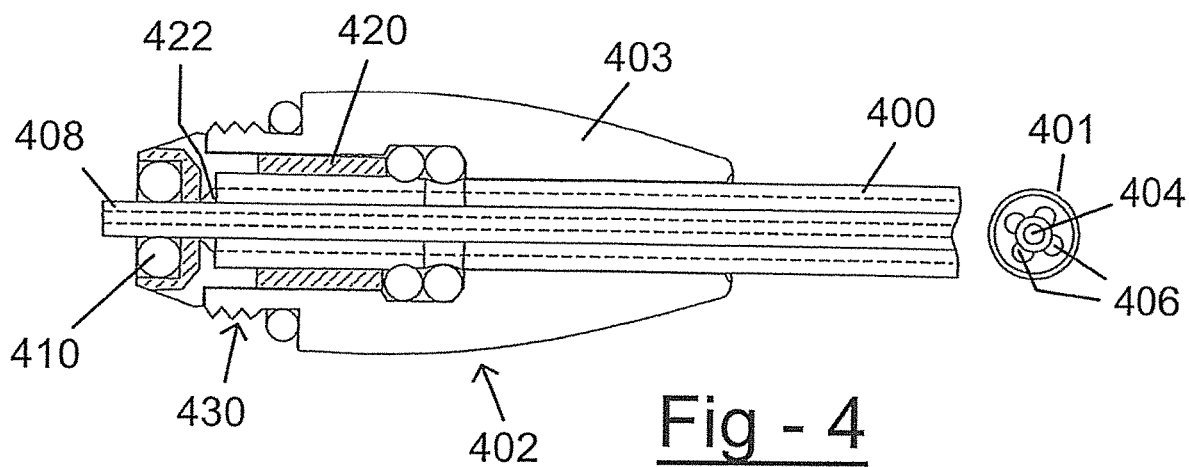
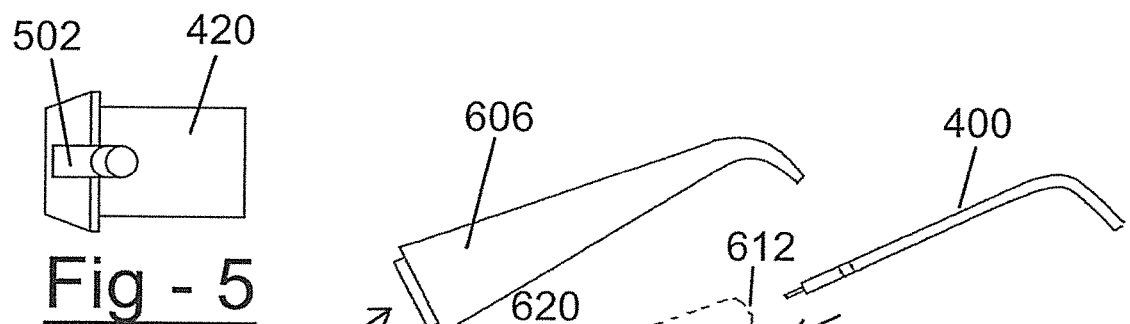
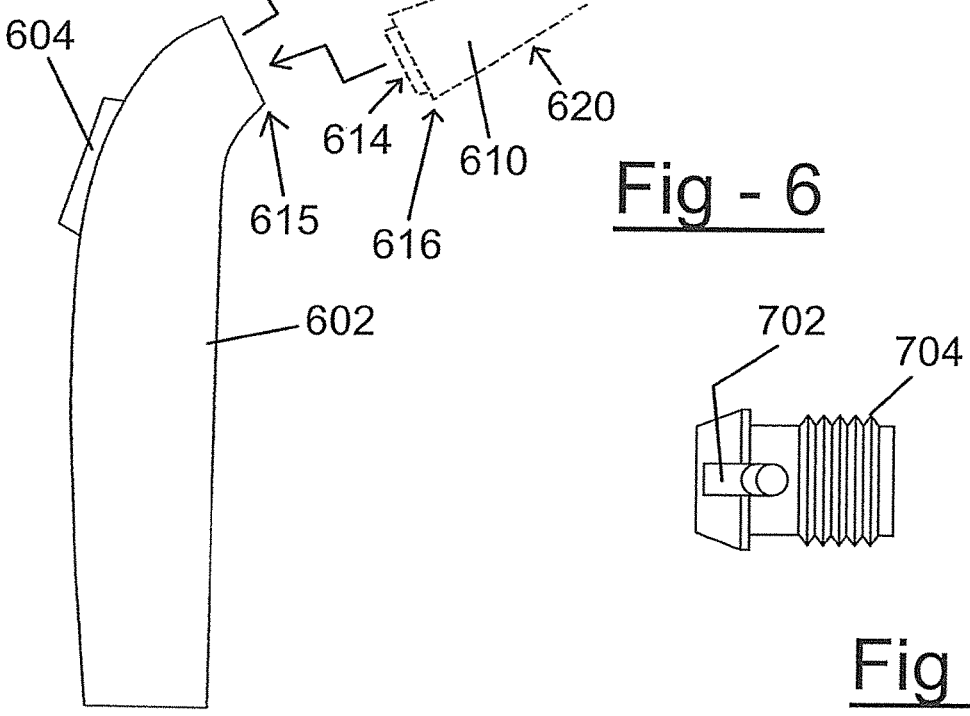

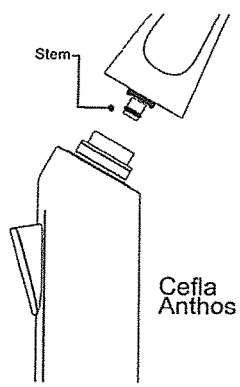
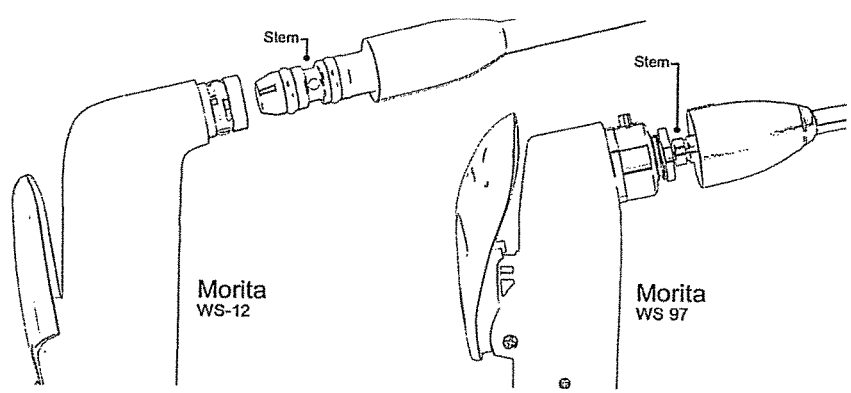
Fig - 10A  Fig - 10B  Fig - 10C
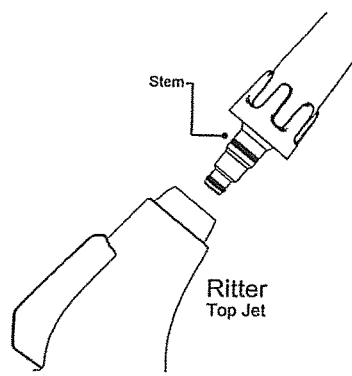
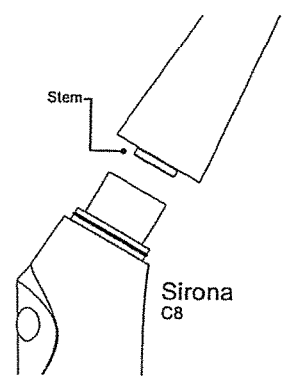
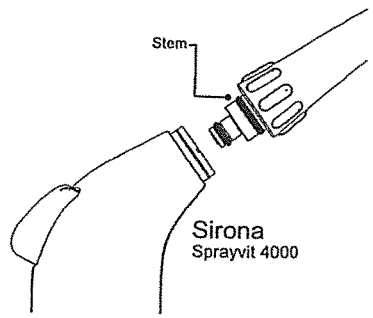
Fig - 10D  Fig - 10E  Fig - 10F
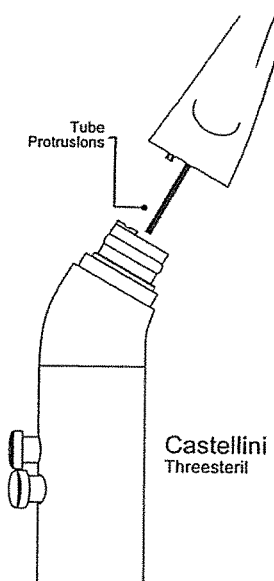
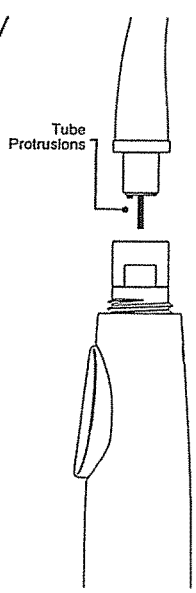
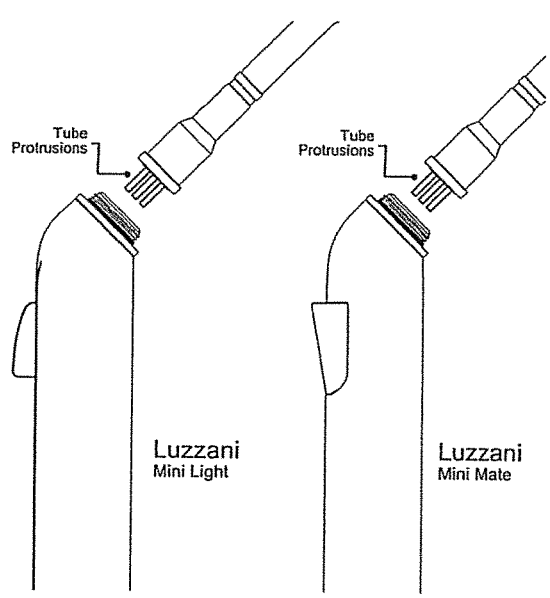
Fig - 11A  Fig - 11B  Fig - 11C  Fig - 11D

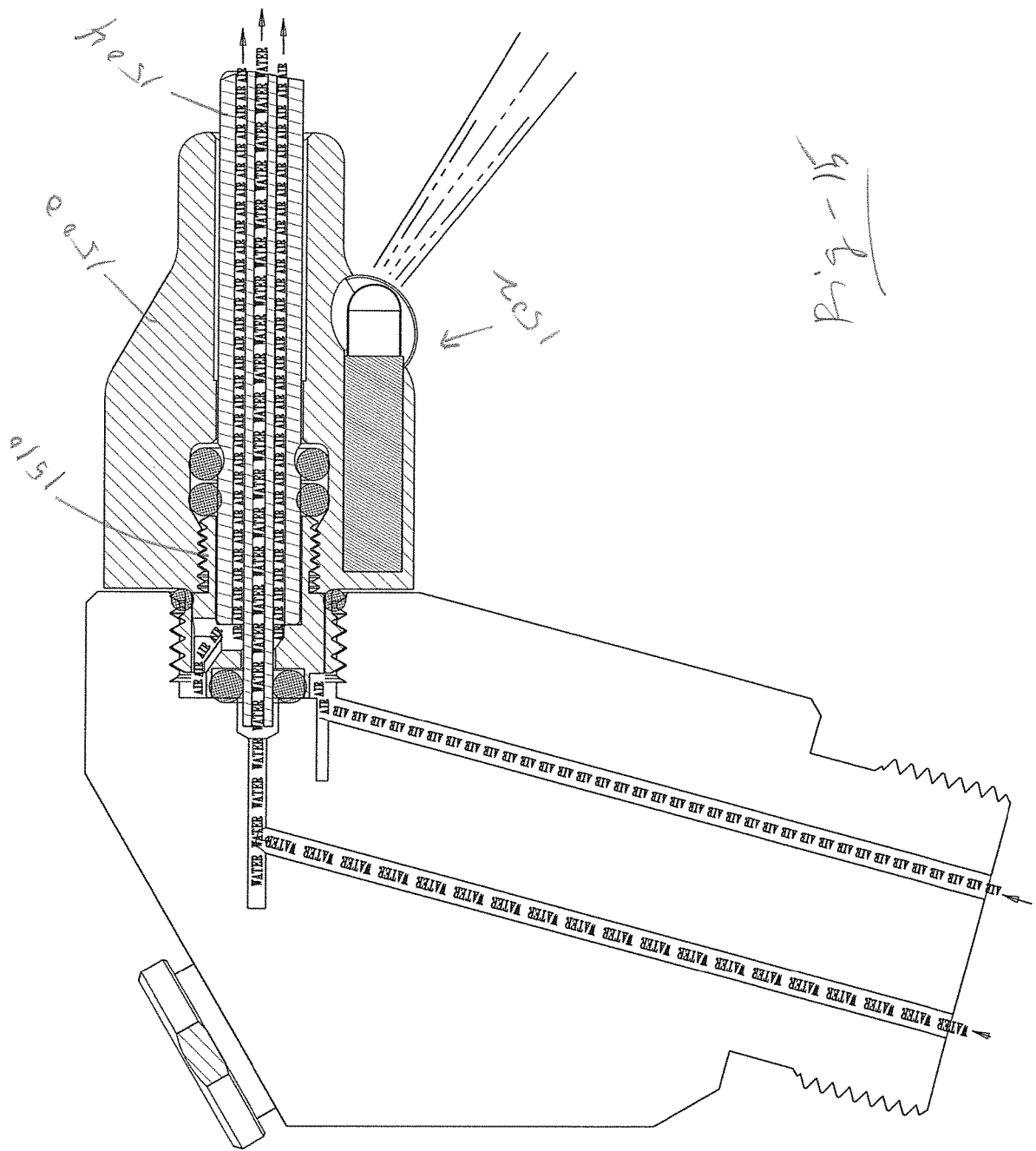

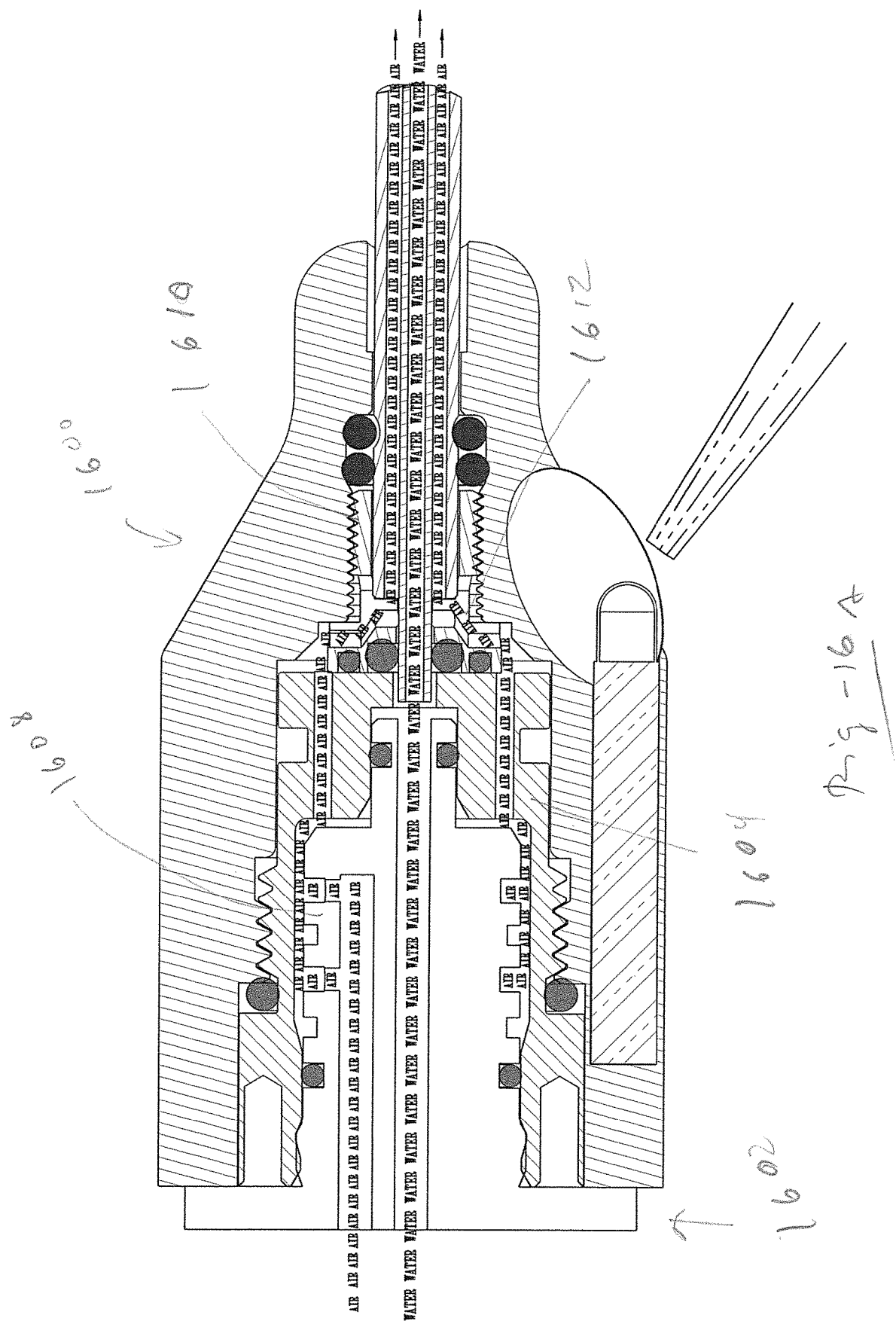

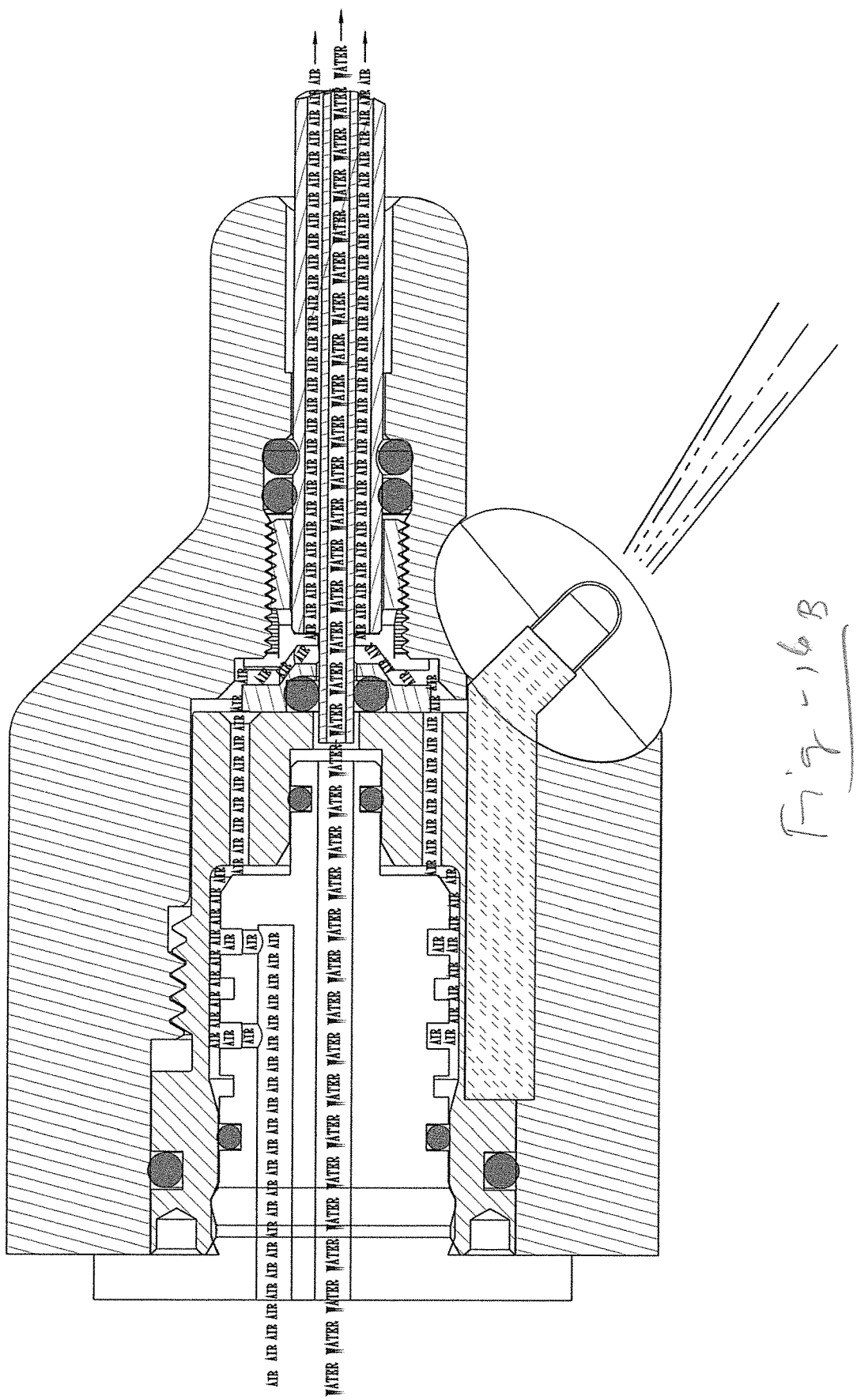

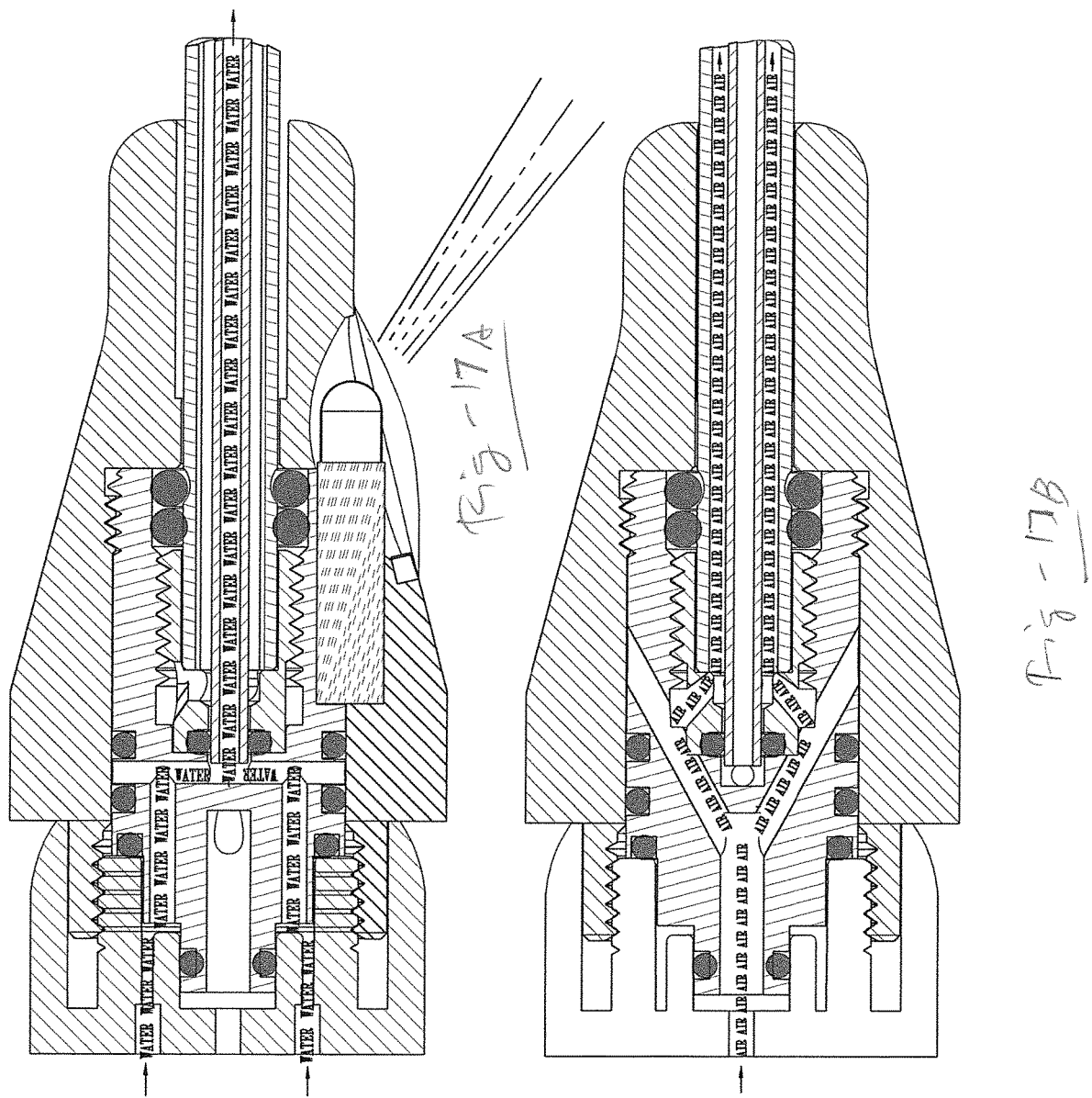

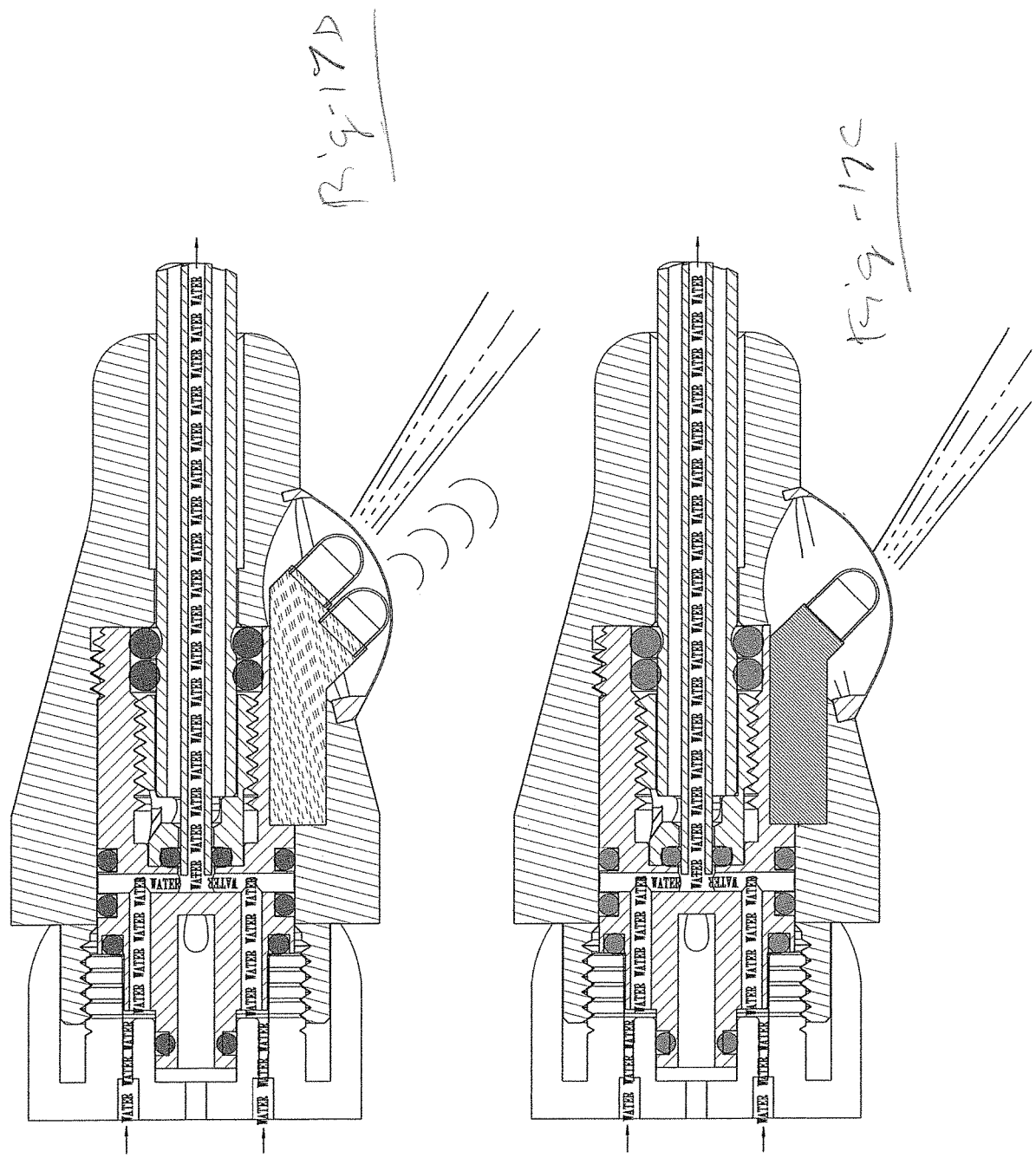

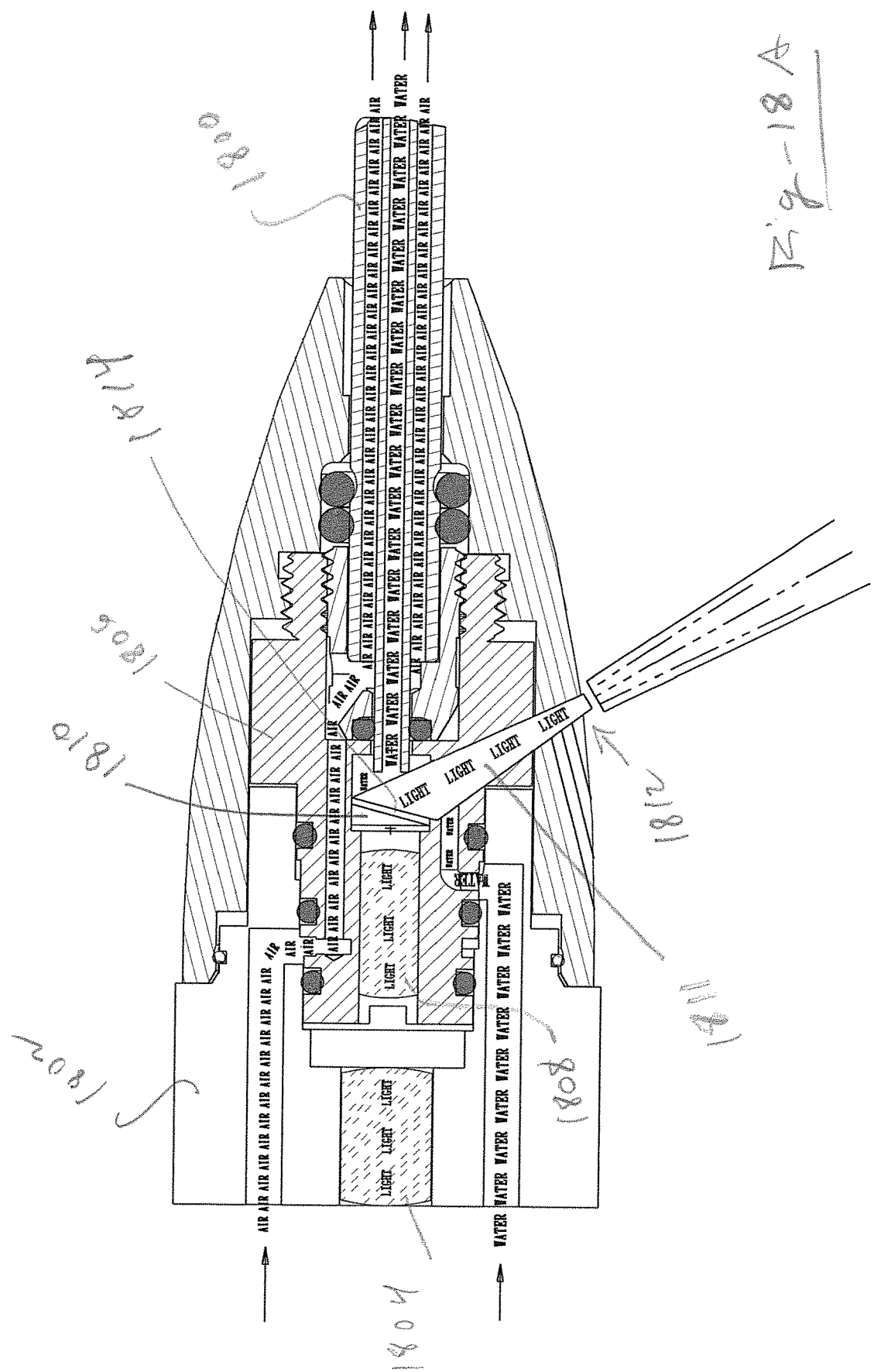

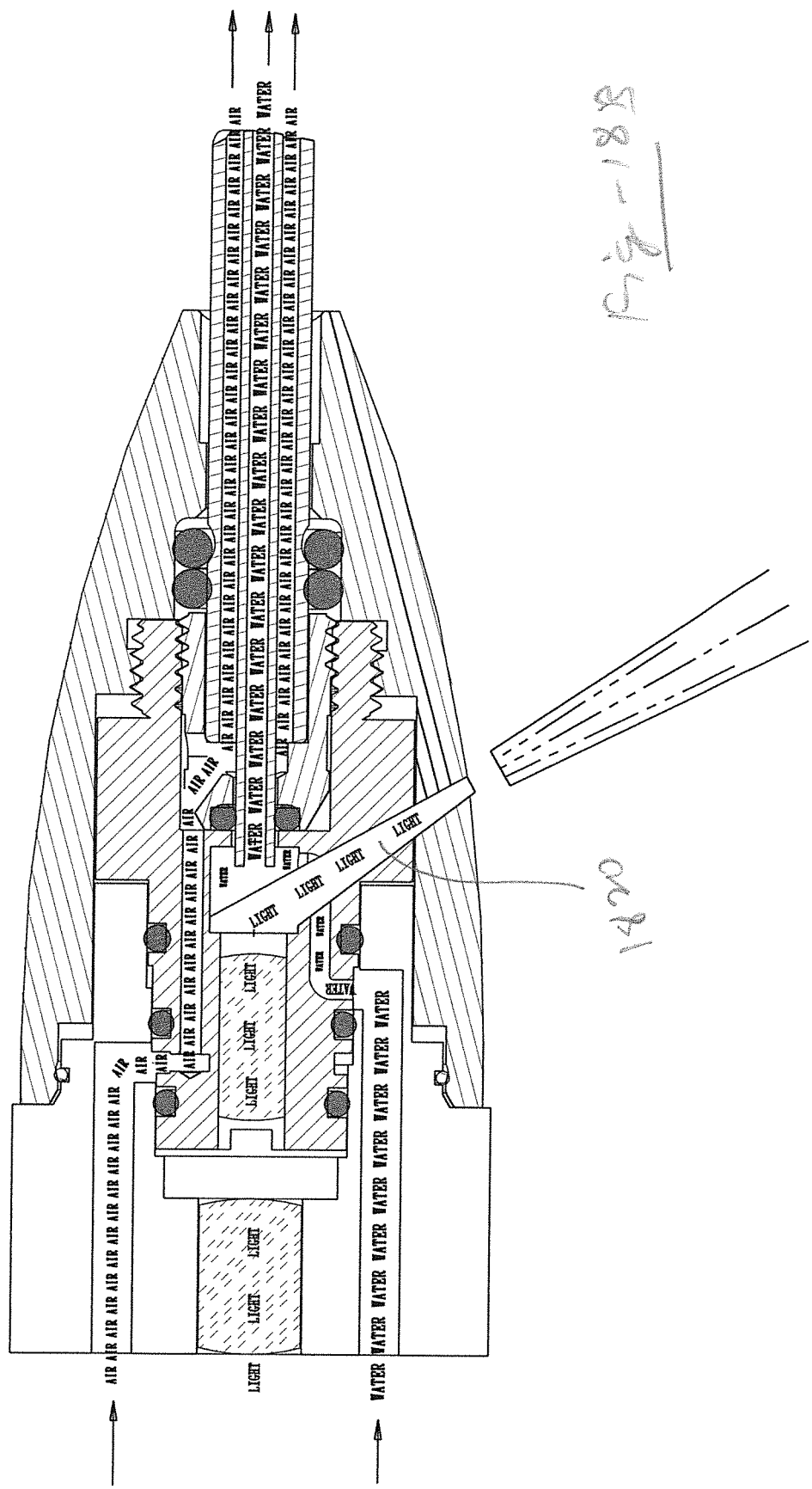

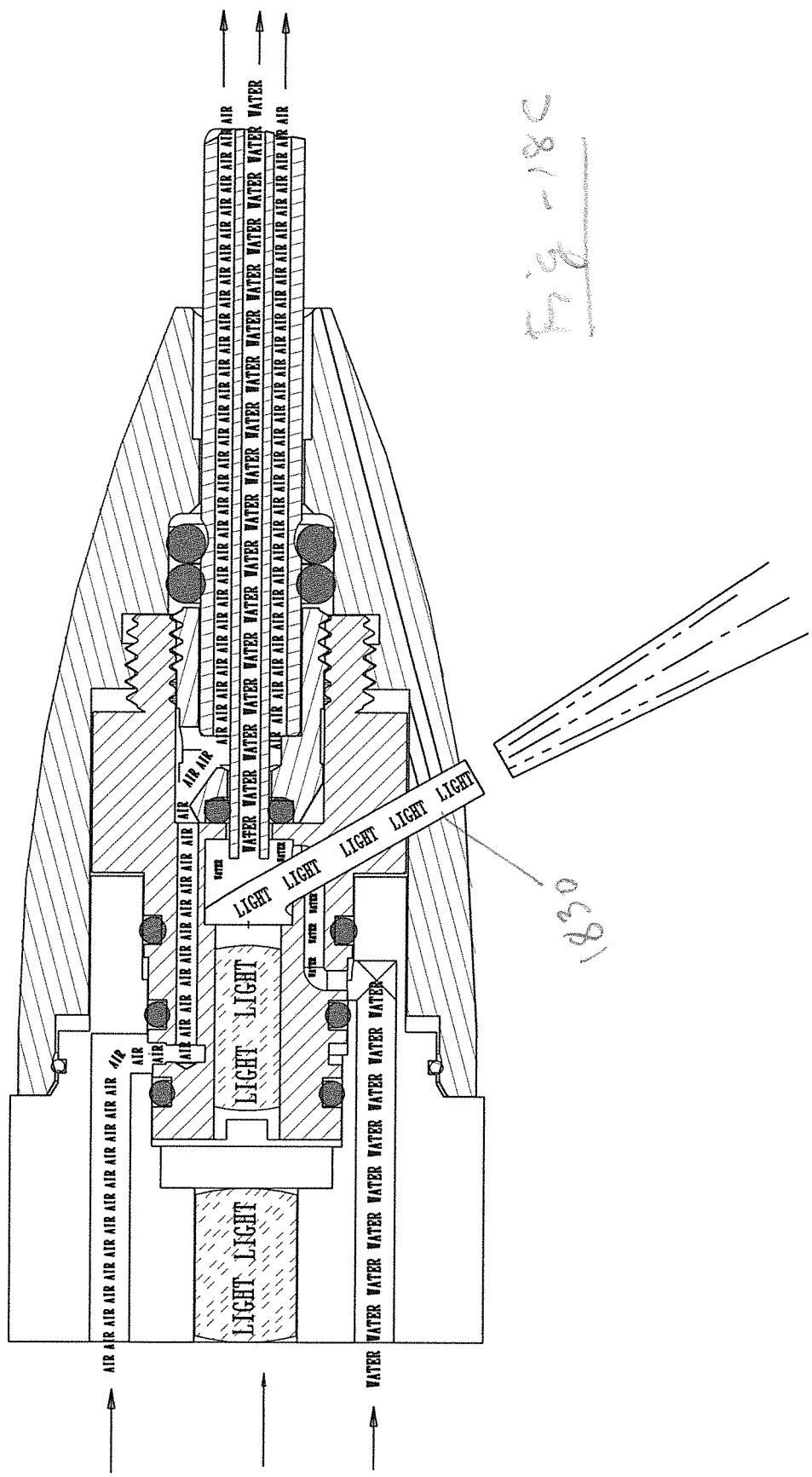

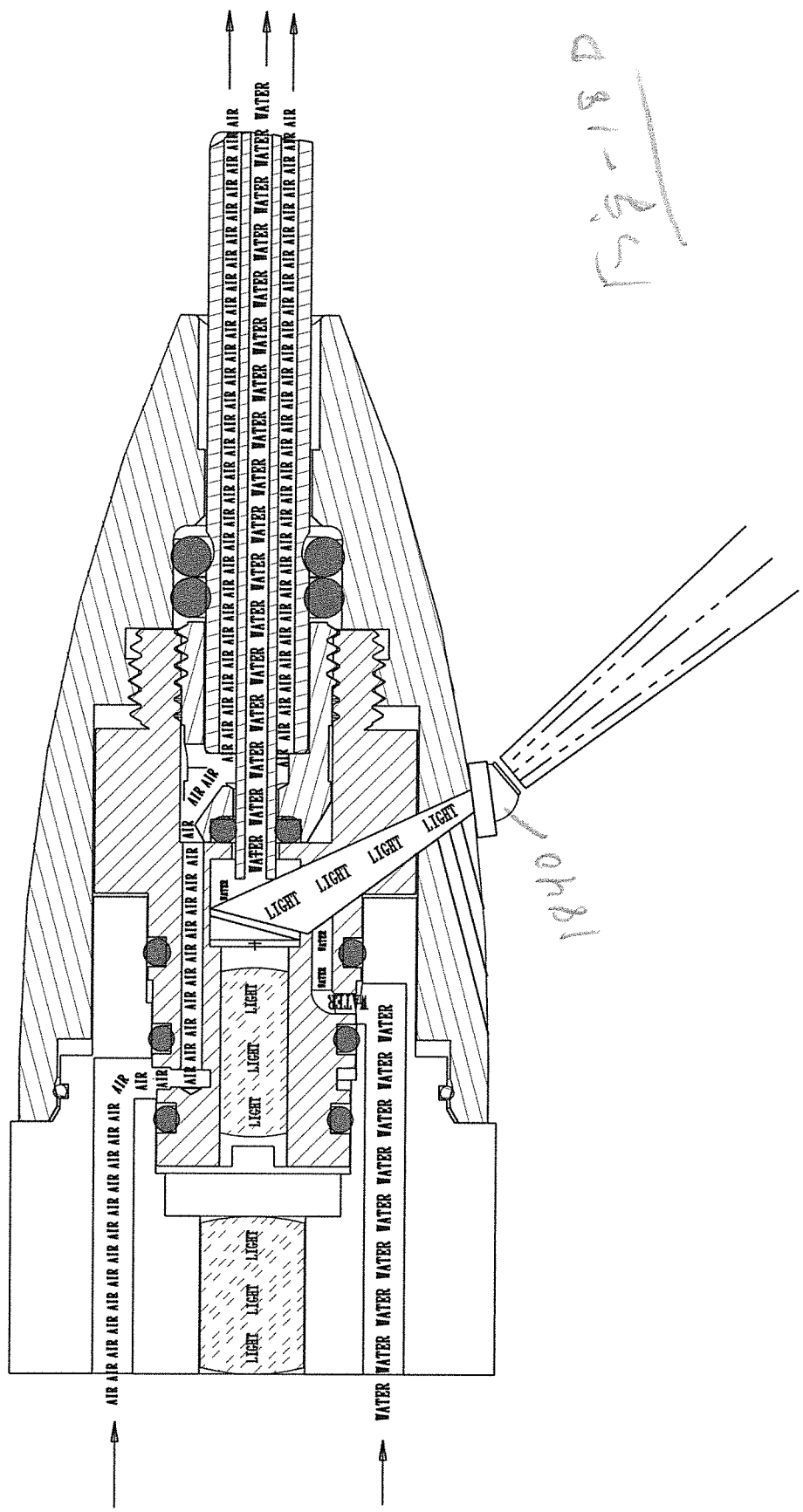

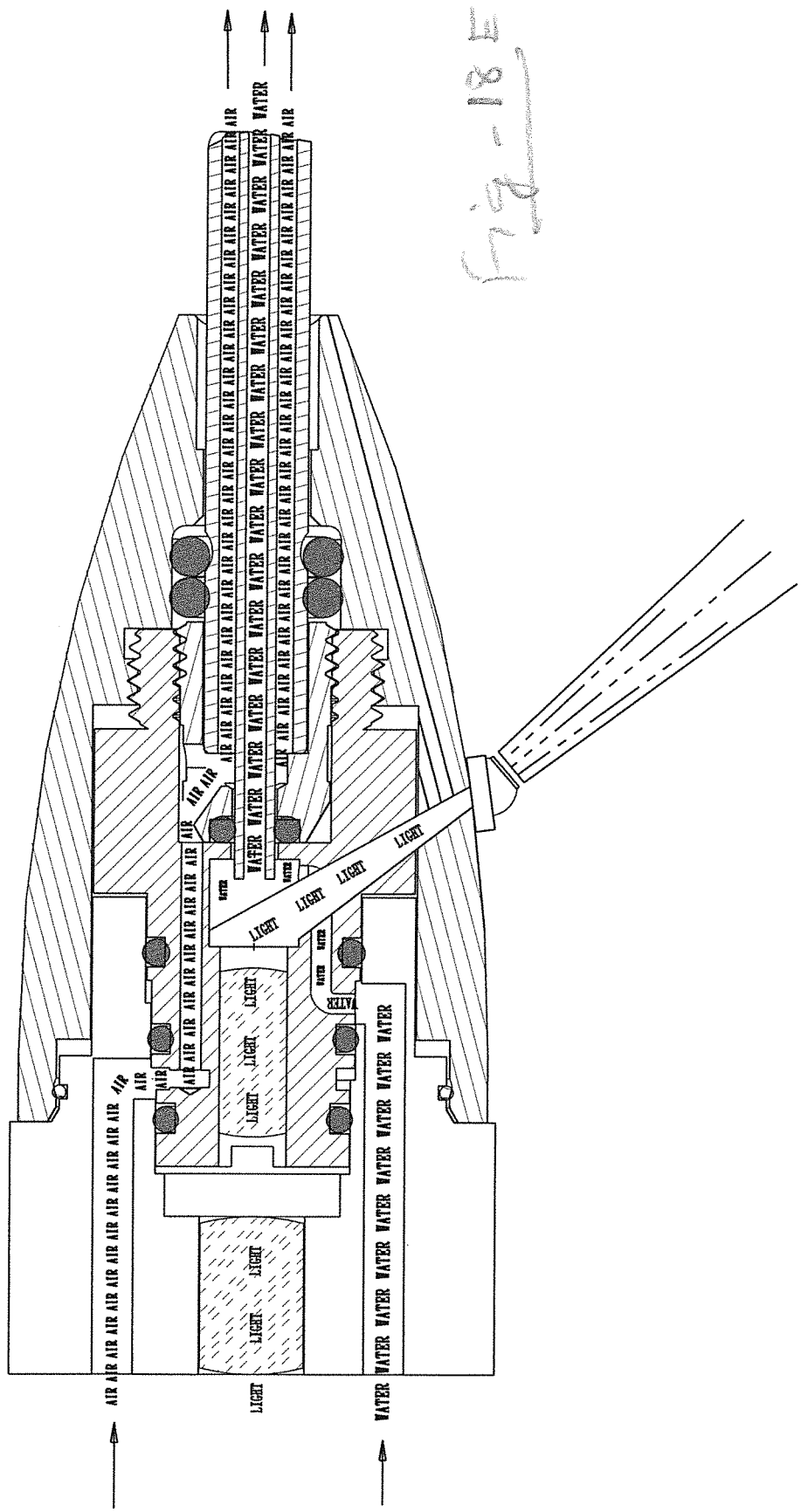

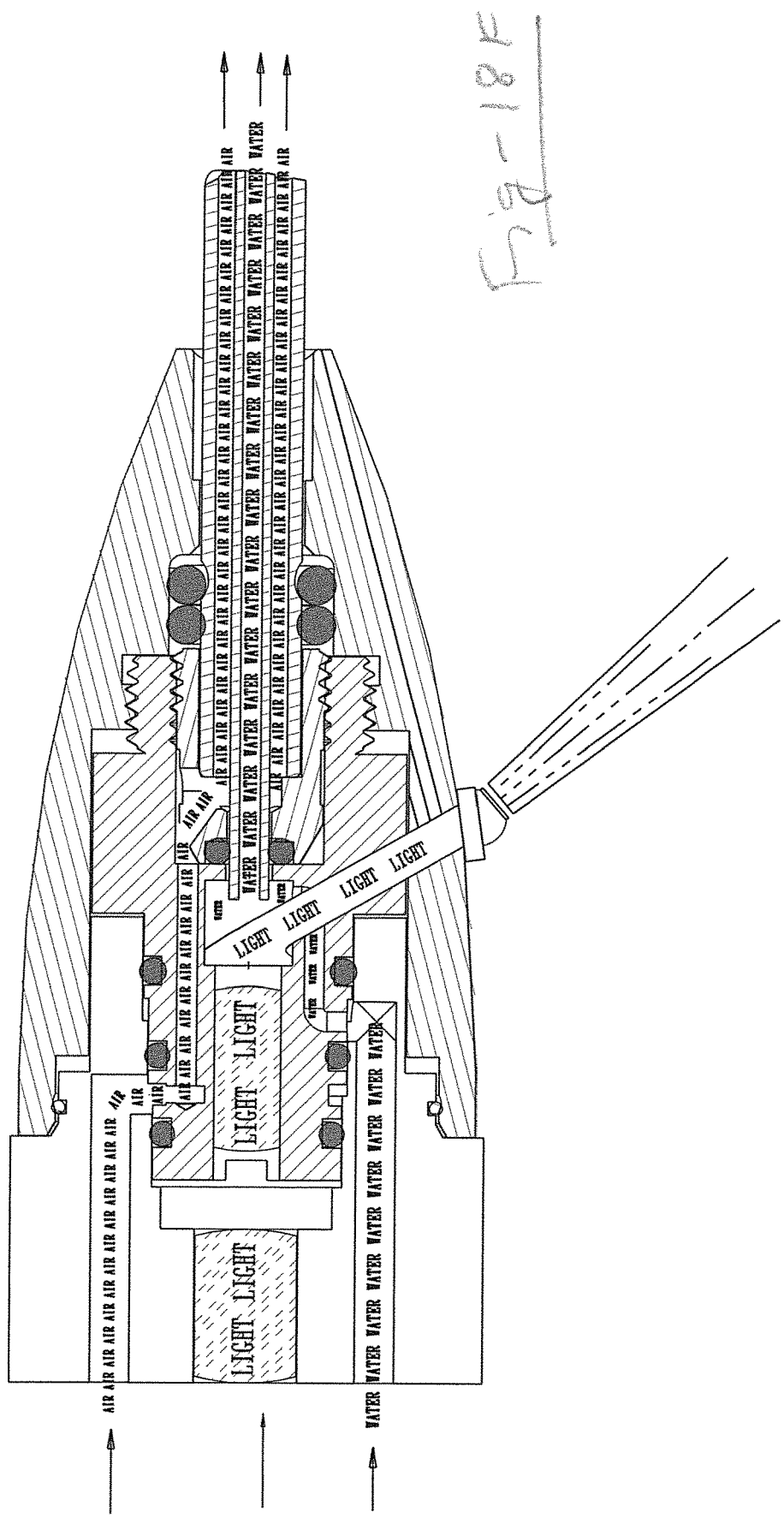

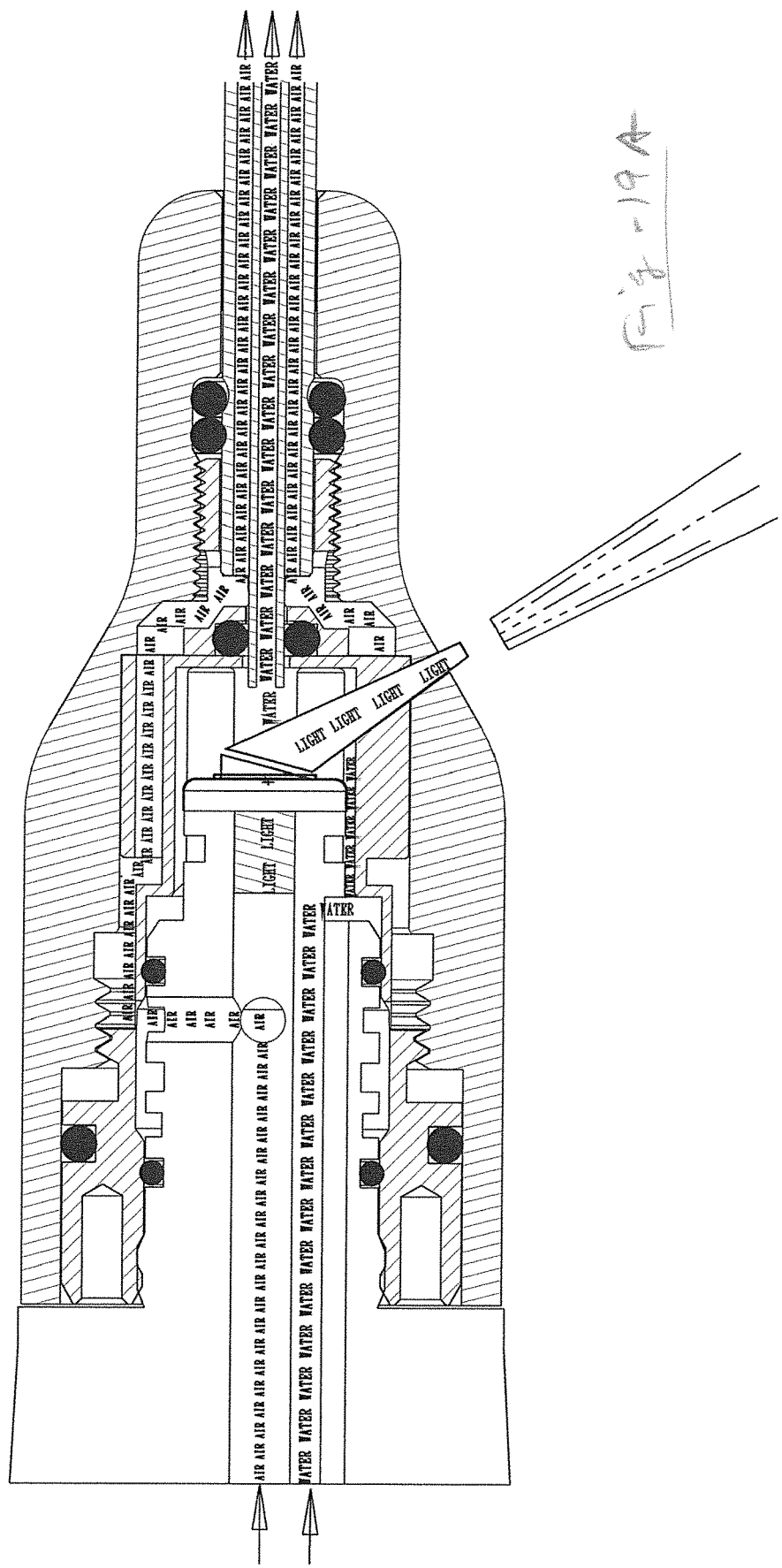

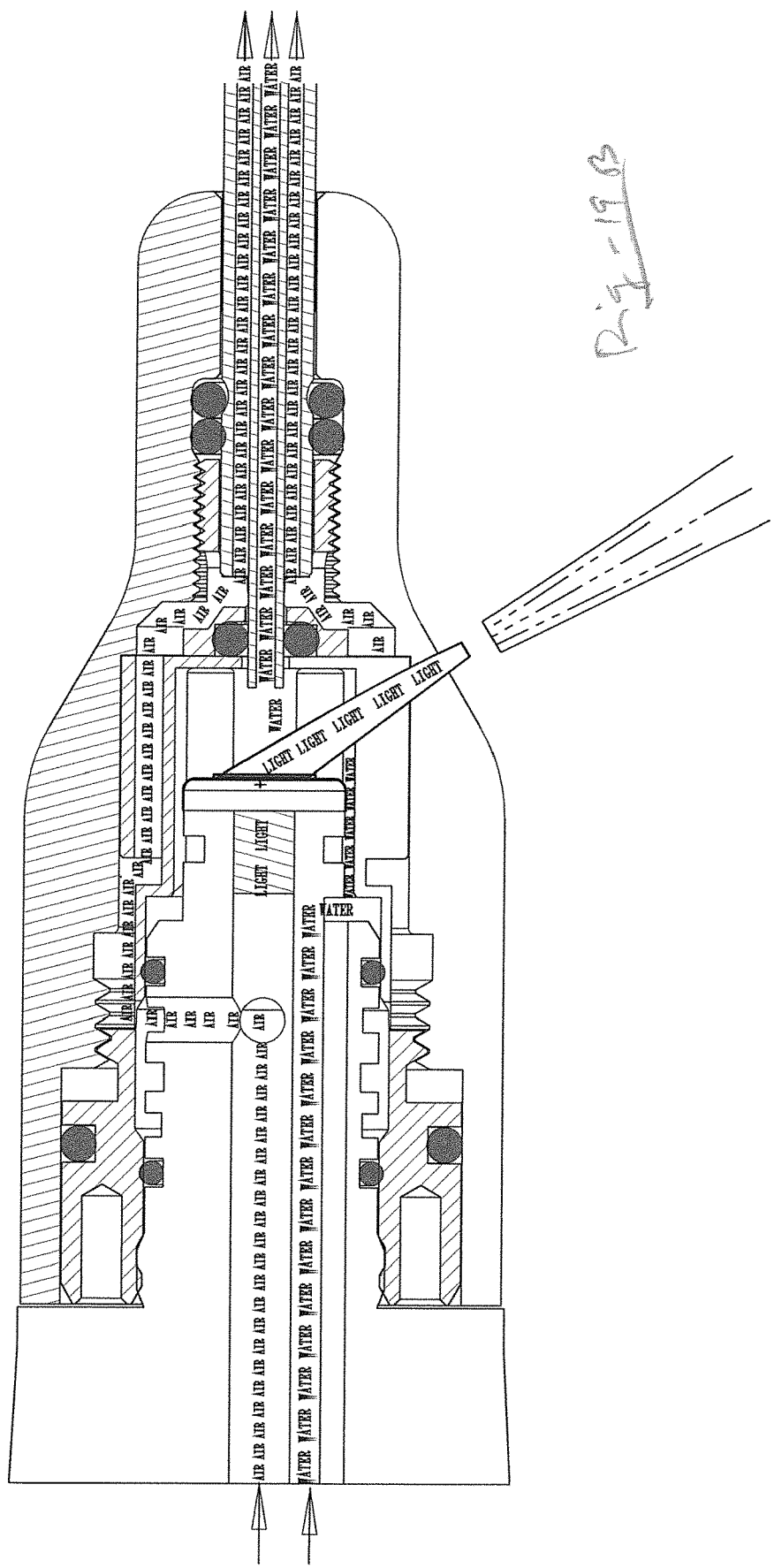

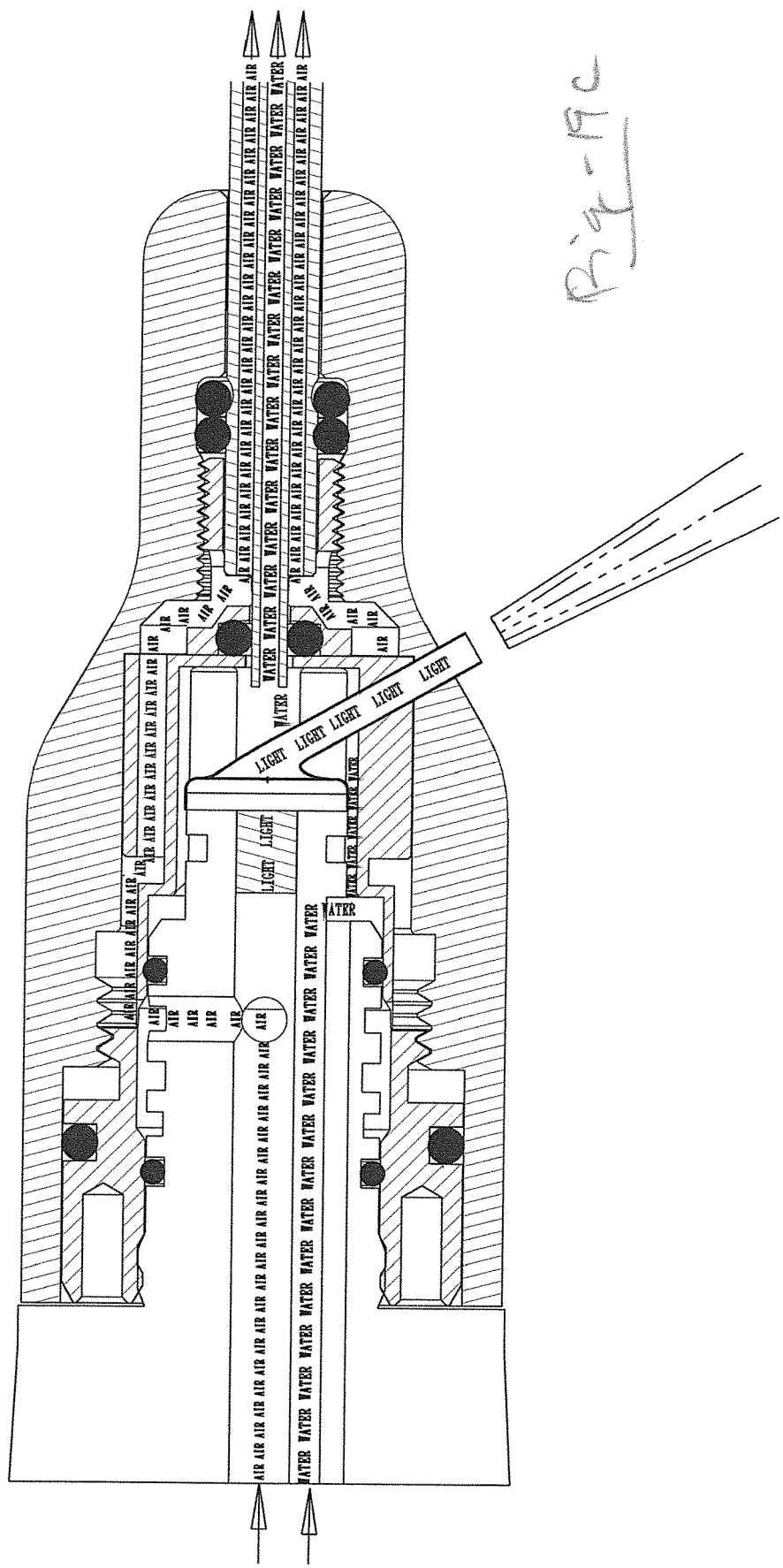

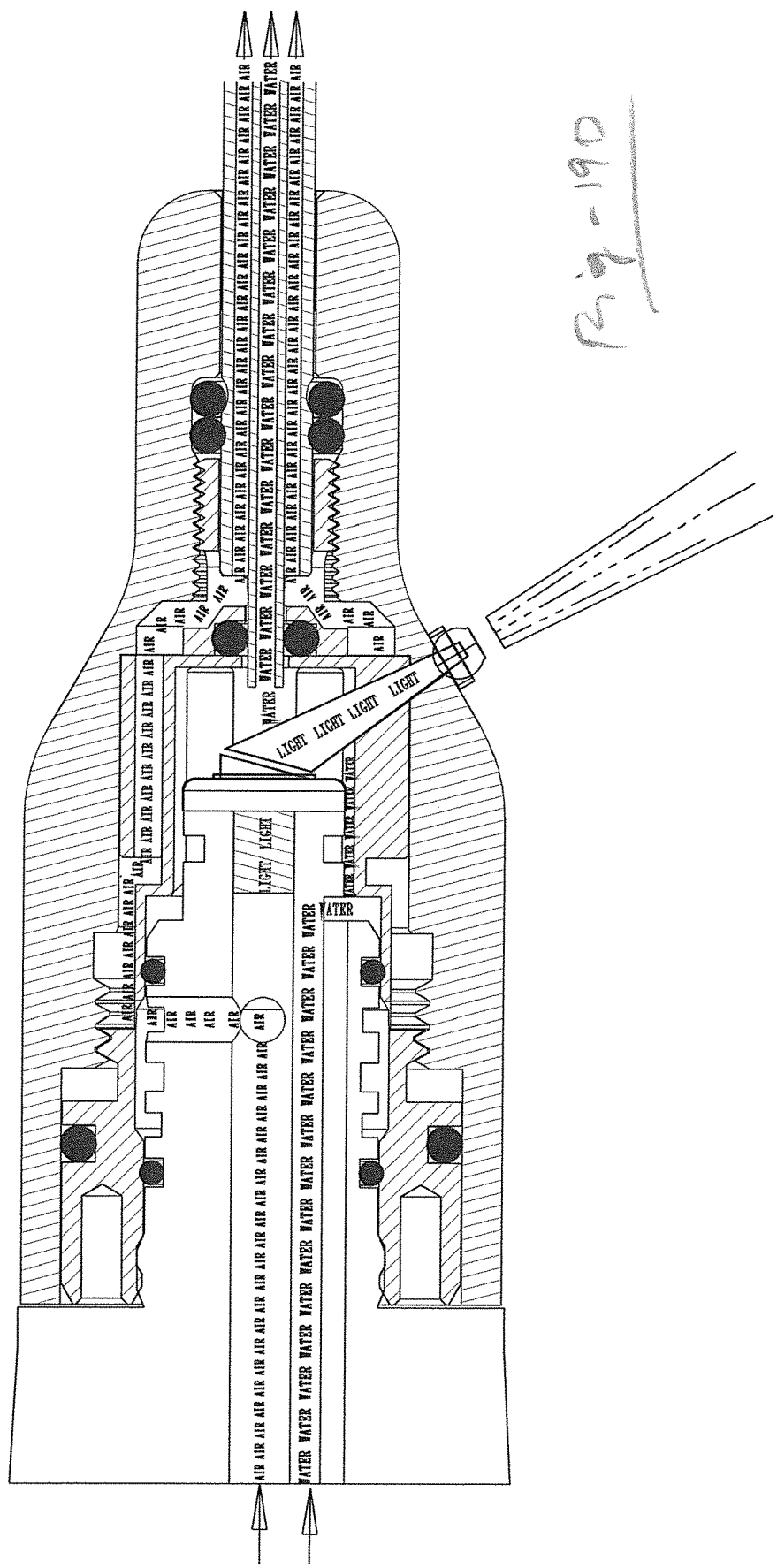

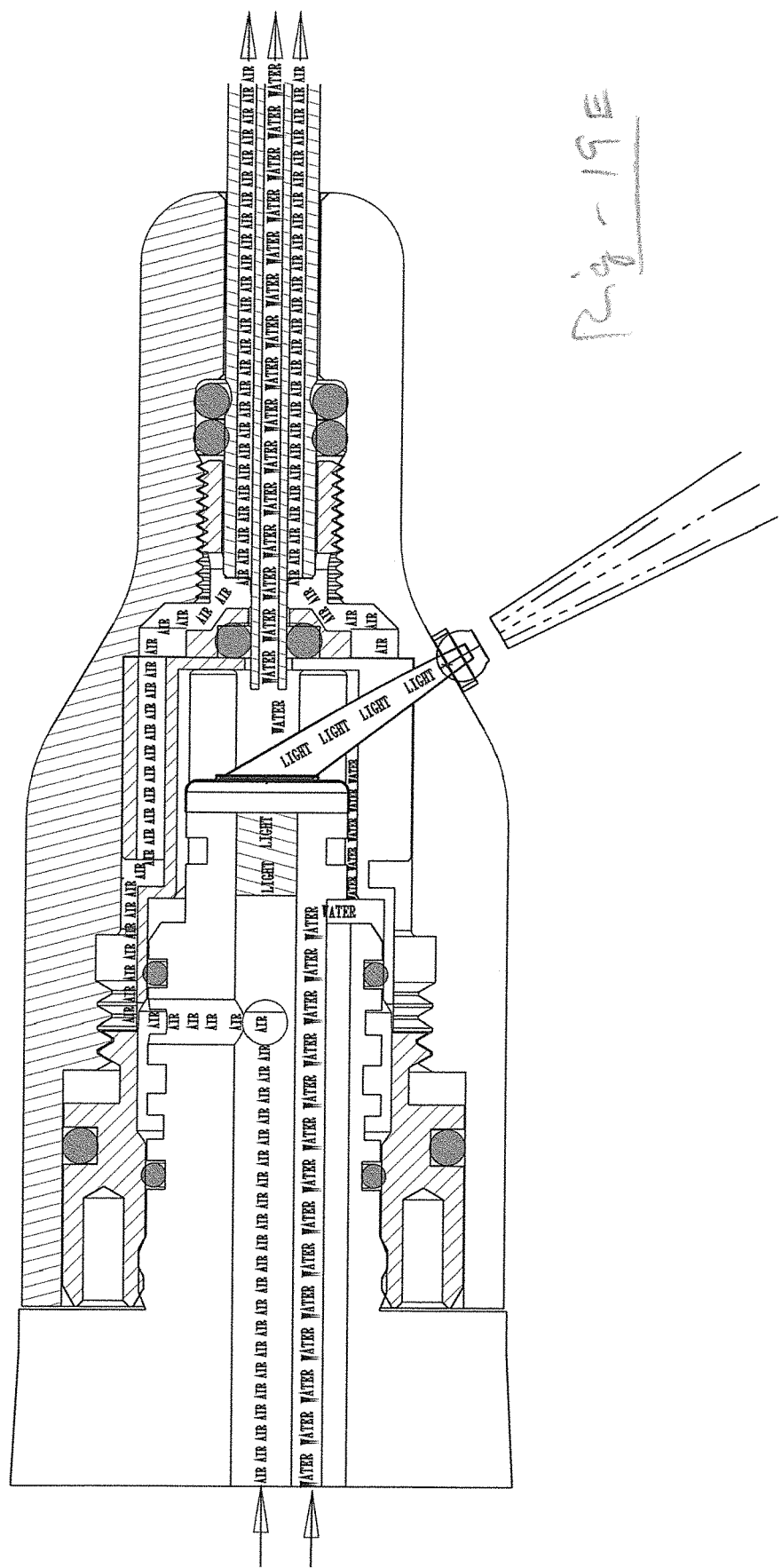

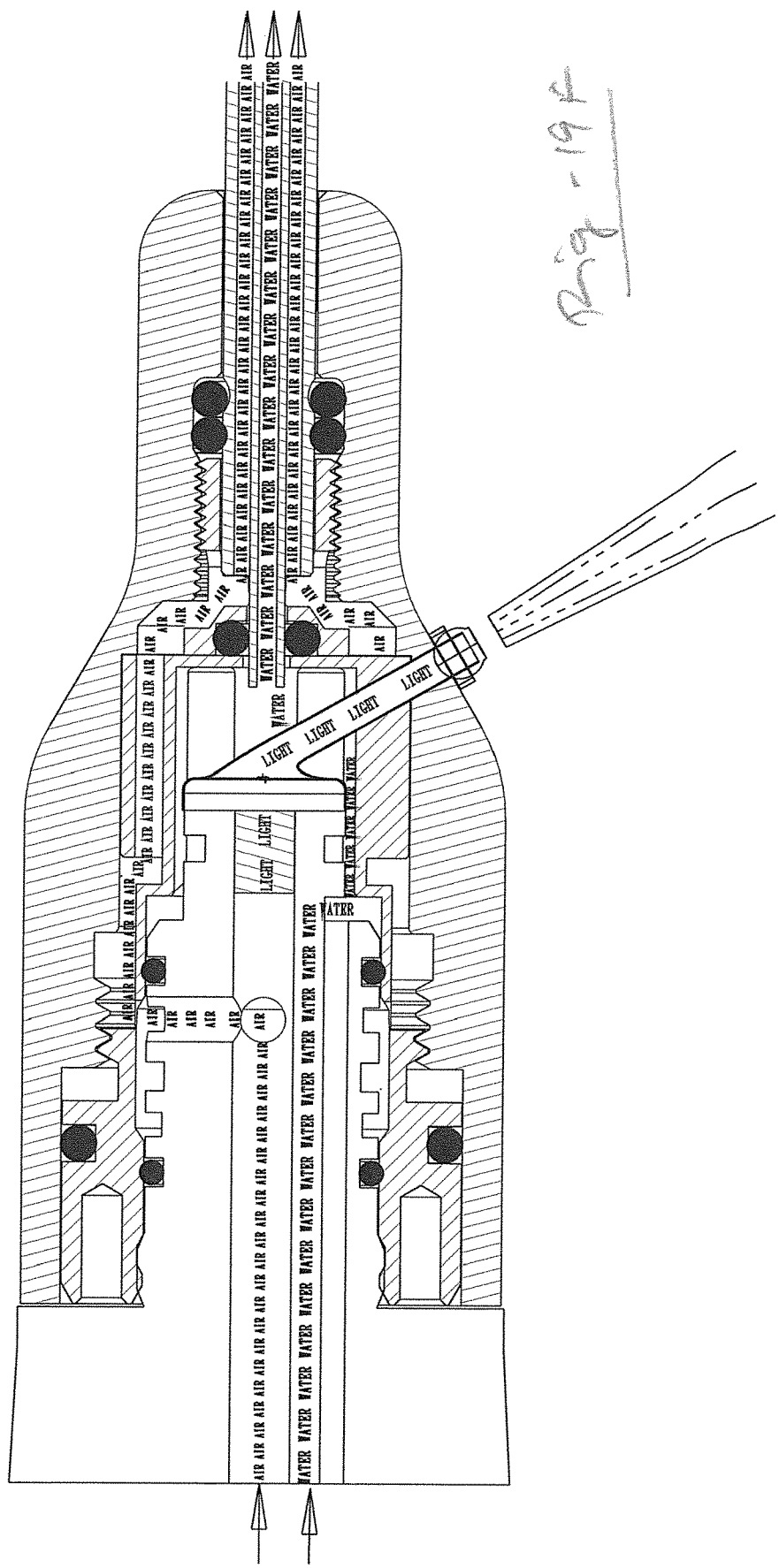

ADAPTERS WITH LIGHT SOURCES FOR DENTAL AIR/WATER SYRINGES

REFERENCE TO RELATED APPLICATIONS

This application is a continuation of U.S. patent application Ser. No. 14/530,380, filed Oct. 31, 2014, which is a continuation-in-part of U.S. patent application Ser. No. 13/907,296, filed May 31, 2013, which is a continuation-in-part of U.S. patent application Ser. No. 13/841,280, filed Mar. 15, 2013, which claims priority from U.S. Provisional Patent Application Ser. No. 61/619,578, filed Apr. 3, 2012. U.S. patent application Ser. No. 14/530,380 also claims priority to U.S. Provisional Patent Application Ser. No. 61/898,605, filed Nov. 1, 2013. The entire content of each application is incorporated herein by reference.

FIELD OF THE INVENTION

This invention relates generally to air/water syringes and, in particular, to adapter units that enable replaceable, disposable tips to be used with various handle assemblies including European style syringes, and which provide built-in light sources and video cameras.

BACKGROUND OF THE INVENTION

Dental syringes are hand-held instruments which deliver water and air under pressure into a patient's mouth for washing and drying purposes. Such instruments are widely used by dentists, orthodontists, oral surgeons, dental hygienists and dental assistants. A typical dental includes a head unit which is coupled to hoses that supply water at about 40 PSI and air at about 80 PSI. An elongated tip coupled to the head unit is inserted into a patient's mouth, and buttons on the head unit are operated to discharge water or air through the distal end of the tip.

Cross contamination is one of the principal problems encountered with dental syringes. Bacteria and viruses can be communicated from patient to patient unless the syringe tip is adequately sanitized. The safest and most desirable approach is to replace the syringe tip from the head after each patient treatment. In addition, it is desirable to be able to replace worn tips or change to tips of different configurations quickly and easily.

Several decades ago, dental syringe tips were not readily removable from the syringe head units. Removal often necessitated the unscrewing of a coupling from the head and the sliding of the coupling off of the tip. Around this time, the tip once removed and the associated coupling were autoclaved. A number of small elastomeric O-rings had to be removed before autoclaving because they could not withstand the heat and pressure of the autoclaving process. The entire process was a time consuming, often frustrating experience.

Around 1980, dental syringe quick-disconnect tips were invented. U.S. Pat. No. 4,248,589, the entire content of which is incorporated herein by reference, discloses a dental syringe that includes a head 10, a coupling 12, and a removable, replaceable tip 14 (FIG. 1). It is important to note that this tip/adapter only fitted 1 syringe at that time—Adec. No other syringe in the world would accept that tip or adapter. The head 10 has internal water and air passages 16 and 18 in communication with an internally threaded cylindrical cavity 22 in the top frontal surface of the head (FIG. 2). The head and tip include a corresponding number of fluid passages. The coupling 12 includes a cylindrical base and a lock nut which screws over the base. The base and the lock nut define an axially extending bore which communicates with the passages through the head and removably receives the rearward portion of the tip 14. An elastomeric O-ring is positioned between the base and the lock nut and surrounds the bore. When the rearward portion of the tip is fully inserted in the bore the O-ring seats in a groove surrounding the rearward portion of the tip. When the lock nut is fully screwed over the base, deformation of the O-ring is substantially prevented and the tip cannot be withdrawn or ejected from the coupling.

The tip 14 comprises inner and outer elongate, coaxial, spaced apart pipes 36 and 38 which define water and air passages 40 and 42, respectively. The forward portions of the pipes are angled with respect to the rearward portions. The forward end 44 of the inner pipe 36 is open and the forward end 46 of the outer pipe 38 is bent inwardly and is sealed to the inner pipe 36. The forward end 46 has a plurality of annularly spaced nozzle apertures such as 48.

The rearward portion 50 of the outer pipe 38 terminates short of the rearward portion 52 of the inner pipe 36 and is bent inwardly and sealed to the rearward portion 52. The rearward end 53 of the inner pipe 36 is open and coaxial with the water passage 16 and abuts the bottom of the cavity 22 when inserted in the coupling 12. The periphery of the rearward portion 50 is formed with a pair of axially spaced, rearward and forward annular grooves 54 and 56. A pair of diametrically positioned inlet apertures 58 and 60 extend through the wall of the outer pipe 38 in the groove 54, as shown in FIG. 3.

Ducts 82 and 84 in the base 62 extend from the bore 72 in the base to a chamber 80. When the rearward portion of the tip is fully inserted in the bore 72, air can flow from the air passage 18 into the chamber 80, through the ducts 82 and 84, into the bore 72, through the apertures 58 and 60, into the air passage 42 and through the tip.

Push buttons 24 and 26 on the top rear surface of the head are coupled to normally closed valves and are selectively hand-operated to discharge water, air, or both through the distal end 28 of the tip 14. A handle 30 can be threaded with the shank 20 to connect water and air supply hoses 32 and 34 to the water and air passages 16 and 18, respectively. When the push buttons 24 and 26 are simultaneously depressed water spray mist is produced.

Since the development of the quick-release syringe tip system just described several improvements have taken place. Central to such improvements is the development of the disposable tip which is retrofittable to the older metal units which must be autoclaved to reuse. Disposable air/water syringe tips resemble bent, plastic straws with multiple cannulations to receive and deliver air and water from existing hand-held units. One leading manufacturer is Crystal Tip of Irvine, Calif.

As with the earlier, autoclavable metal syringe tips, the proximal end of the Crystal Tip includes a central, protruding tube to receive water which, like its predecessors, seals against an O-ring in the syringe body. However, as shown in FIG. 4, the tip does not have proximal side ducts through which the air flows; rather the proximal end surrounding the water tube does not 'bottom out' within the syringe body, allowing air to enter the cannulations surrounding the central water tube. Crystal Tips are designed to be used directly on common U.S. and Canadian syringes. In particular, Crystal Tips fit syringes from Adec (Newberg, Oreg.), DCI International (Newberg, Oreg.) and Unic/Heka (Ishøj, Denmark) without the need for any so-called adapter units.

Currently in Europe, however, most syringes use autoclavable tips. As a result, there has been little attempt to upgrade to new standards that have been in place for years. As such, disposable tips, including Crystal Tips, cannot be used directly on any European syringe. Syringes with autoclavable tips use a variety of routing patterns to deliver air and water to the tip. However, all U.S. disposable tips receive their air flow through the base of the tip that is inserted into the syringe. Autoclavable tips route air flow through a side port (hole) directly below an O-ring grove on the metal tip. As such, without some type of conversion, disposable tips are incompatible with European-style syringes that use autoclavable tips.

Given that there are numerous proprietary designs outside North America, it would be advantageous to provide these syringes with appropriate adapter kits enabling them to utilize standard, disposable quick-release air/water tips.

U.S. patent application Ser. No. 13/841,280, filed Mar. 15, 2013, discloses numerous conversion kits enabling disposable tips to be used on multiple different syringe bodies, including European designs that use autoclavable tips. However, the embodiments described in this previous application use two subassemblies—a cap subassembly that receives the disposable tip, and an adapter subassembly that couples the cap to the syringe body after the non-disposable or autoclavable tip has been removed.

The cap subassembly 402, shown in FIG. 4, includes an outer body 403 with a distal end to receive the tip 400 and a proximal end configured to receive a ferrule 420 shown in FIG. 5. The ferrule includes a cup-shaped receptacle that receives the proximal end of the disposable tip once inserted into the cap body 403. The disposable tip is shown in FIGS. 4 and 6 at 400. View 401 is an end view showing the central water-carrying tube 404 surrounded by air-carrying channels 406. In the tip shown, a Crystal Tip from Westside Resources of Irvine, Calif., the water tube protrudes from the proximal end of the tip at 408, facilitating an additional O-ring seal at 410 for enhanced air/water separation. The proximal end of tip 400 includes a tapered region to ensure that the tip end does not "bottom out" against the bottom of the ferrule cup. This allows air to flow through side grooves 502 and into the air-carrying channels 406 of the tip. Again, however, as long as access to the air-carrying channels is provided, such a tapered region is not necessarily required.

SUMMARY OF THE INVENTION

This invention resides in adapter units enabling a disposable tip to connect to an existing dental syringe configured to receive a different type of tip such as an autoclavable tip. In addition, adapter units constructed in accordance with this invention provide built-in light sources and/or video camera units, thereby providing the syringe bodies to which the adapters attach capabilities that they could not have without the adapters.

A conversion kit according to the invention includes a retainer body having an outer surface and a proximal end that attaches to a dental syringe providing air and water. The retainer body further includes a distal opening into which the proximal end of an elongated disposable tip is inserted, the disposable tip having a central, water-carrying tube surrounded by air-carrying channels terminating in a distal end. One or more components within the retainer body have cut-outs, grooves or channels to direct the air and water from the syringe body to the air-carrying channels and water-carrying tube of the disposable tip.

A self-contained module, removably coupled to the retainer body, includes a light-emitting diode (LED), a battery powering the LED, and a switch to turn the LED ON and OFF, the LED generating light generally proximally toward the distal end of the disposable tip. In the preferred embodiments, the retainer body includes a cavity into which the self-contained module is removably received. The conversion kit may further include a lens to direct light from the LED toward the distal end of the disposable tip following insertion into the retainer body.

In addition to a manually operated ON/OFF switch, the fluid going thru the nozzle or the tip or thru the adapter may act as an ON/OFF circuit. For example, the water in the syringe going thru the adapter may power a micro turbine that would also power the LED. The ON/OFF switch may be in electrical communication with a touch panel on the outer surface of the retainer body used to turn the switch ON and OFF. Alternatively, the switch may be in electrical communication with a motion detector disposed within the self-contained module, whereby the detection of motion turns the LED ON, and the absence of motion for a predetermined period of time turns the LED OFF.

An optional, miniature video camera may also be disposed in the self-contained module, the camera being powered by the battery and controlled by the switch. This embodiment may include an electronic interface enabling the video information to be retrieved from the module for further recording or display purposes. Alternatively, a wireless transmitter may be disposed in the self-contained module, with a receiver for receiving video information from the camera through the wireless transmitter for further recording or display purposes. In all embodiments, the video camera may have a field of view corresponding to the light generated by the LED light source.

BRIEF DESCRIPTION OF THE DRAWINGS

FIG. 1 is an exploded isometric view of a prior art dental syringe showing its quick-release tip withdrawn;

FIG. 2 is an enlarged side elevational view of the dental syringe of FIG. 1 with portions broken away;

FIG. 3 is a sectional view taken along line 3-3 of FIG. 2;

FIG. 4 is a drawing in partial cross section showing an existing cap subassembly and disposable tip;

FIG. 5 is a side view of a ferrule used in the cap subassembly of FIG. 4, showing side grooves configured for the passage of air;

FIG. 6 is an exploded view illustrating how the invention replaces an autoclavable tip on a generic, European-style with a conversion kit and disposable tip;

FIG. 7 is a side view of a threaded ferrule constructed in accordance with the present invention, also including side grooves configured for the passage of air;

FIGS. 10A-10F illustrate syringe systems to which the invention is applicable that feature stems protruding from the removed tip and into the syringe body;

FIGS. 11A-11D illustrate syringe systems to which the invention is applicable that feature tube projections from the removed tip and into the syringe body;

FIG. 15 is a cross section of an adapter with an LED light source for an ADEC syringe;

FIG. 16A is a cross section of an adapter with an LED light source for a KAVO K4 syringe;

FIG. 16B is a cross section of an adapter with an angled LED light source for a KAVO K4 syringe;

FIG. 17A is a cross section of an adapter with an LED light source for a CGE syringe;

FIG. 17B is a different cross section of the adapter of FIG. 17A illustrating air and water channels;

FIG. 17C is a cross section of an adapter with an angled LED light source for a CGE syringe;

FIG. 17D is a cross section of an adapter with an LED light source and optional camera for an ADEC syringe;

FIG. 18A is a cross-sectional drawing showing a Sirona syringe wherein light is brought in via optical conduit;

FIG. 18B shows how a two-piece prism may be replaced with a single-piece light guide;

FIG. 18C illustrates the alternate use of an optical fiber;

FIG. 18D shows a component that rotates or swivels to direct the light to a desired location;

FIG. 18E shows the component of FIG. 18D used with a single optical light guide;

FIG. 18F shows the component of FIG. 18D used with an optical fiber or conduit; and FIGS. 19A-19F depict the use of an adapter that receives a disposable tip for use in conjunction with a Kayo model syringe which includes a fiber optic light source.

DETAILED DESCRIPTION OF THE INVENTION

Figure 8A:
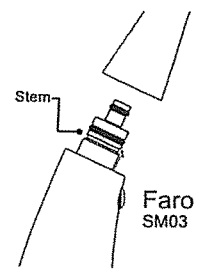
FIGS. 8A-8G illustrate syringe systems to which the invention is applicable that feature stems protruding from the syringe body.
Figure 8B:
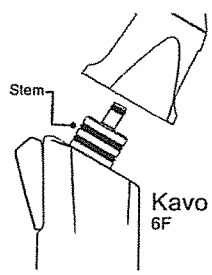
Figure 8C:
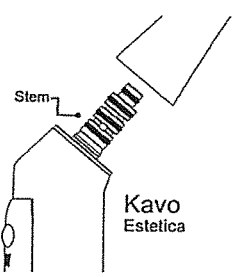
Figure 8D:
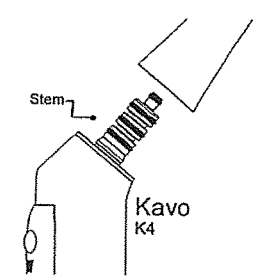
Figure 8E:
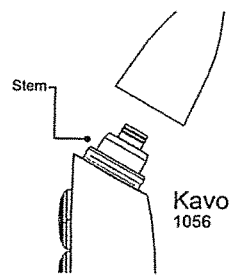
Figure 8F:
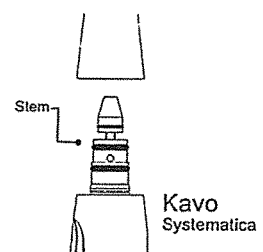
Figure 8G:
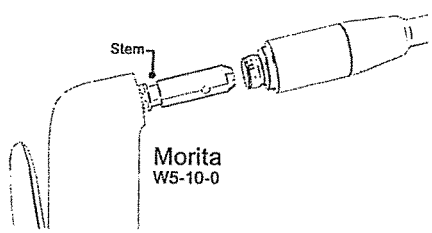

This invention improves upon existing air/water syringe instrumentation by providing conversion kits that enable replaceable, disposable tips to be used with various syringe assemblies, including European-style syringes. The invention is also applicable to disposable tips with disposable tips having extended proximal water tubes as well as tips with flush air/water passages on opposing flat proximal and distal ends. Nor is the invention limited in terms of the number of air-carrying channels surrounding the central water-carrying tube. The invention is further not limited in that addition to air and/or water gels, abrasives, other liquids or materials used in dental procedures may be accommodated.

FIG. 6 is a simplified drawing showing a generic syringe body 602 with air/water control buttons 604. The figure also shows a generic autoclavable tip 606 which is removed from the body 602 and replaced with a retainer body 610 having a distal end 612 to receive disposable tip 400. The retainer is illustrated in broken-line form because it is a generic example with specific embodiments being described below with respect to detailed cross-sectional drawings. In all embodiments, however, air/water directing components internal to the retainer are installed through a proximal opening 614 in the retainer, such that the proximal portion 616 of the retainer can be flush against a corresponding portion 618 of the syringe body so that the outer surface 620 of the retainer can be smooth and seamless from the syringe to the distal end 612.

Figure 9A:
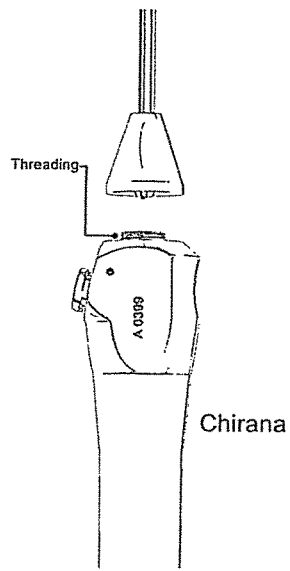
FIGS. 9A-9C illustrate syringe systems to which the invention is applicable that feature threaded connections between the syringe body and the tip which is removed.
Figure 9B:
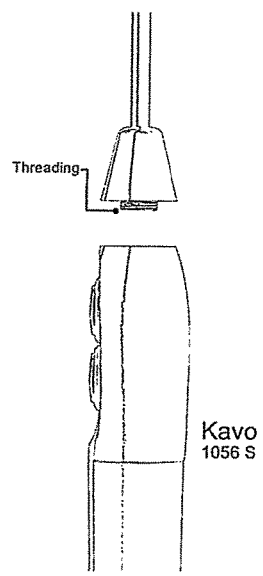
Figure 9C:
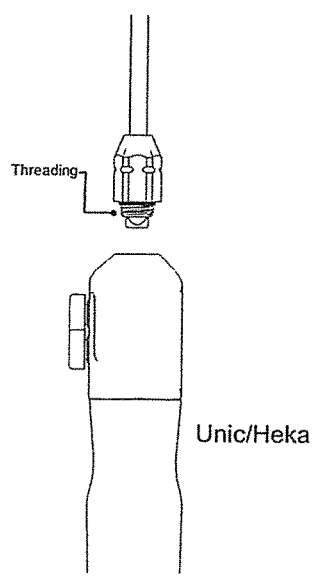

The components associated with the retainer body span a range of parts and complexity depending upon the type of syringe and the tip being replaced. That said, the invention accommodates all current styles and may be extended to yet-to-be developed designs with appropriate engineering modification. In particular, the invention includes conversion kits with retainers and components to accommodate syringe systems with stems that protrude from the syringe body, as exemplified in FIGS. 8A-8G; syringe systems that feature threaded connections between the syringe body and the tip without any prominent protrusions, as depicted in FIGS. 9A-9C; syringe systems with stems protruding from the removed tip, as shown in FIGS. 10A-10F; and syringe systems that feature tube projections from the removed tip, as shown in FIGS. 11A-11D.

One component internal to the retainer body is a cup-shaped ferrule to receive the proximal end of the disposable tip once inserted into the distal end of the retainer. Such a ferrule, shown in FIG. 5, includes a central opening through which water passes into the water-carrying tube of the disposable tip and one or more side cut-outs 502 through which air passes into the air-carrying channels of the disposable tip. The ferrule 420 further includes a central opening to receive a water-carrying tube extending from the proximal end of the disposable tip. As with the other components internal to the retainer body, the ferrule is installed through the proximal opening in the retainer. FIG. 7 shows a different ferrule with side cut-outs 702, but which is threaded at 704 to maintain its position.

Figure 12A:
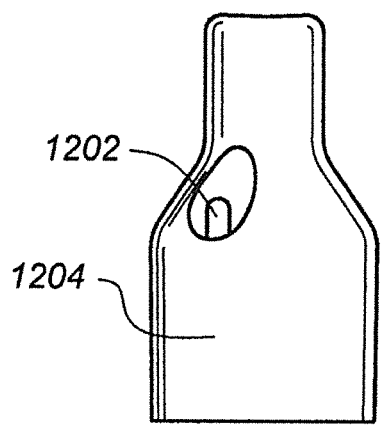
FIG. 12A is a side view of an embodiment of the invention wherein an LED light is disposed on an outer retainer of an adapter.
Figure 12B:
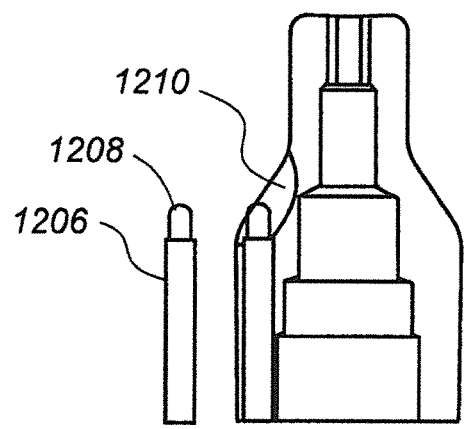
FIG. 12B is a cross section of the embodiment of FIG. 12A.

FIG. 12A is a side view of an embodiment of the invention wherein an LED light 1202 is disposed on an outer retainer 1204 of an adapter. FIG. 12B is a cross section of the embodiment of FIG. 12A, showing the LED as part of a module 1206, preferably with a generally cylindrical body to frictionally fit into a cylindrical bore made in the body of the adapter retainer. The self-contained module 1206, removably coupled to the retainer body, includes a light-emitting diode (LED), a battery powering the LED, and a switch 1214 to turn the LED ON and OFF. The assembly may further include a lens 1210 to direct light from the LED toward the distal end of the disposable tip following insertion into the retainer body.

The ON/OFF switch may be in electrical communication with a touch panel on the outer surface of the retainer body used to turn the switch ON and OFF. Alternatively, the switch may be in electrical communication with a motion detector 1216 disposed within the self-contained module, whereby the detection of motion turns the LED ON, and the absence of motion for a predetermined period of time turns the LED OFF.

Figure 13A:
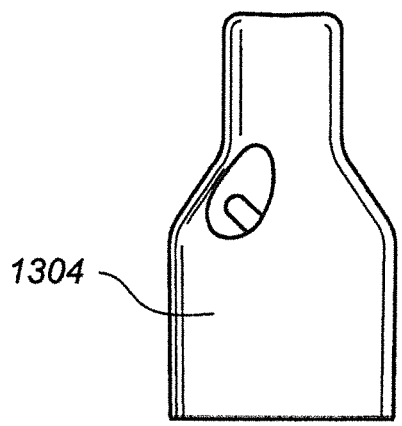
FIG. 13A is a side view of an embodiment of the invention wherein an LED light is attached to an inner sleeve of an adapter.
Figure 13B:
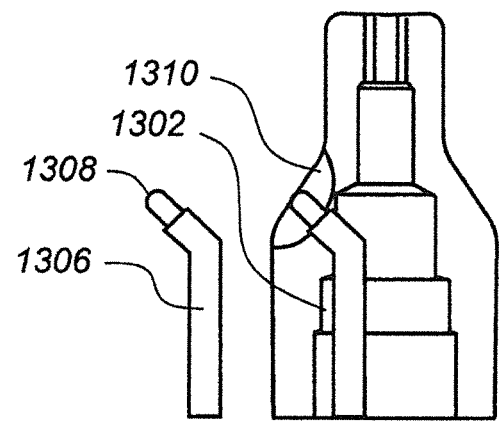
FIG. 13B is a cross section of the embodiment of FIG. 13A.

FIG. 13A is a side view of an embodiment of the invention wherein an LED light module 1306 is attached to an inner sleeve 1302 of an adapter 1304. FIG. 13B is a cross section of the embodiment of FIG. 13A. In this case the module 1306 may be curved or bent, and may include a lens 1210 to direct light from the LED toward the distal end of the disposable tip following insertion into the retainer body.

Figure 14A:
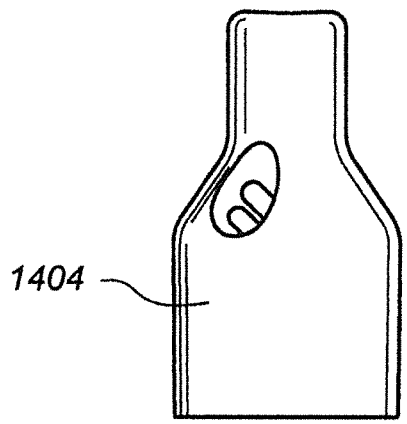
FIG. 14A is a side view of an embodiment of the invention wherein an LED light an optional camera are attached to an inner sleeve of an adapter.
Figure 14B:
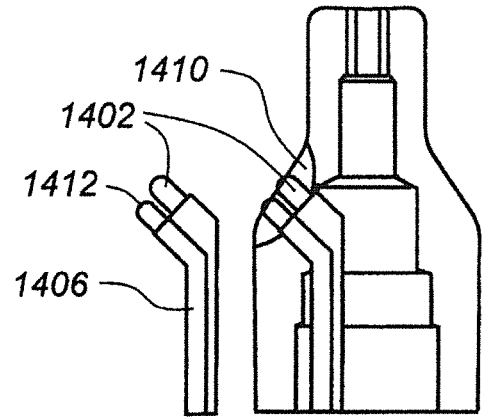
FIG. 14B is a cross section of the embodiment of FIG. 14A.

FIG. 14A is a side view of an embodiment of the invention wherein an LED light and optional camera 1412 are attached to an inner sleeve of an adapter. FIG. 14B is a cross section of the embodiment of FIG. 14A. In this case as well the module 1406 may be curved or bent, and may include a lens 1410 to direct light from the LED toward the distal end of the disposable tip and to image the distal tip with the camera.

The optional, miniature video camera is also be disposed in the self-contained module, the camera being powered by the battery and controlled by the switch. This embodiment may include an electronic interface enabling the video information to be retrieved from the module for further recording or display purposes. Alternatively, a wireless transmitter 1218 may be disposed in the self-contained module, with a receiver for receiving video information from the camera through the wireless transmitter for further recording or display purposes. In all embodiments, the video camera may have a field of view corresponding to the light generated by the LED light source.

FIGS. 15 to 17 are detailed cross-sectional drawings that show conversion kits for particular syringe styles and, in some cases, modified ferrules depending upon the design requirements. In these drawings, the existing syringe body is shown without cross-hatching, whereas the cap and adapter subassemblies are cross-hatched. Air and water flows are also illustrated with text in each cross section. All conversion kits further include multiple O-rings, depicted as black circles. In terms of materials, the ferrules are preferably constructed of a brass alloy to achieve demanding tolerances, whereas the other hard components may be constructed of aluminum or hard plastic. Although certain of the conversion kits provide three or more components in addition to the O-rings, those of skill in the art will recognize that fewer pieces may be used through appropriate machining. For example, the ferrule and end cap may be formed of an integral unit by machining a single piece of brass or aluminum. While such fabrication may complicate the manufacturing process somewhat, the end result eliminates O-rings and simplifies assembly by the user.

FIG. 15 is a cross section of an adapter with an LED light source 1502 for an ADEC syringe. Ferrule 1510 screws into the retainer body 1500. The disposable tip is depicted at 1504.

Figure 16C:
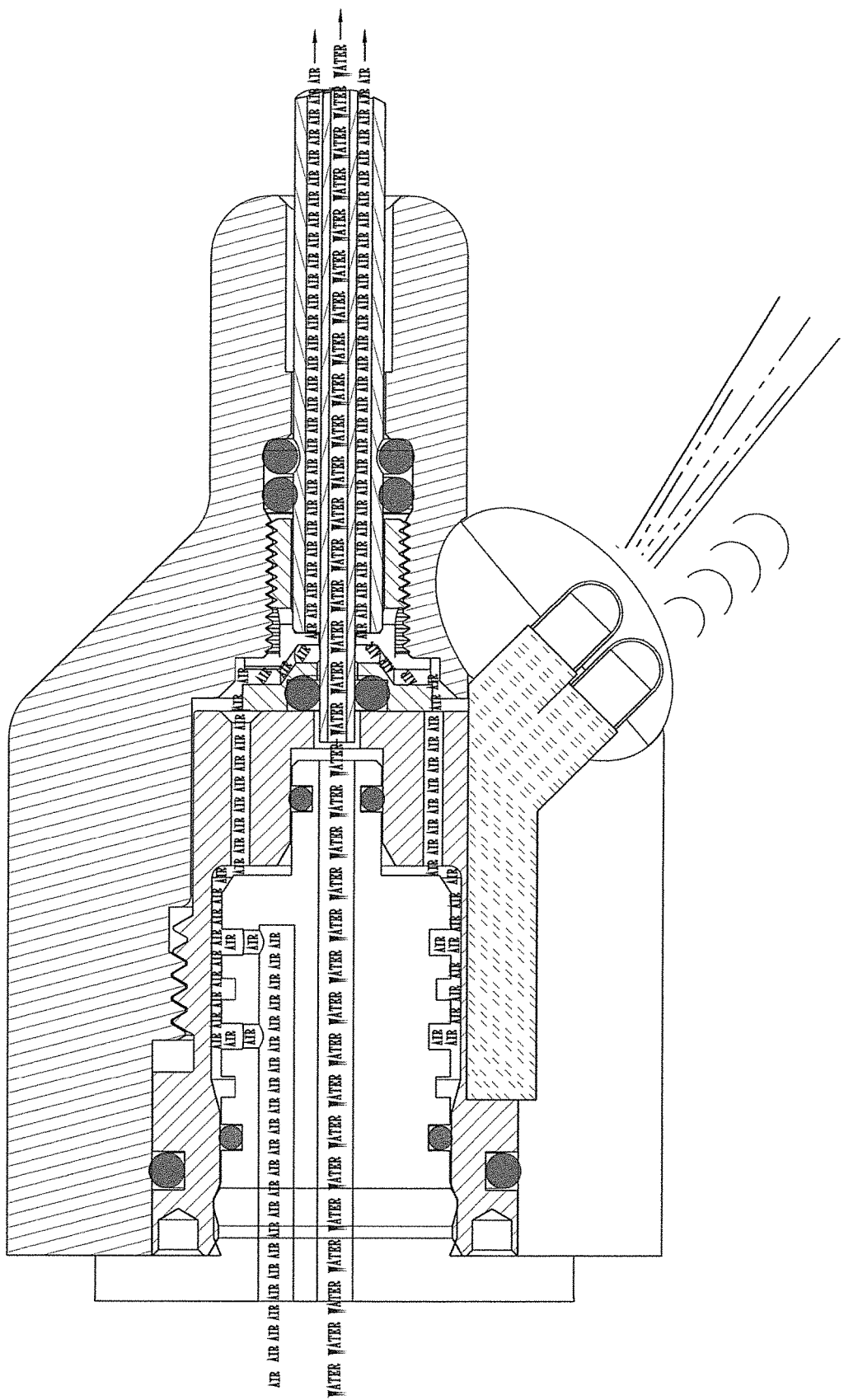
FIG. 16C is a cross section of an adapter with an LED light source and optional camera for a KAVO K4 syringe.

FIG. 16A is a cross section of an adapter with an LED light source for a KAVO K4 syringe. FIG. 16B is a cross section of an adapter with an angled LED light source for the KAVO K4, and FIG. 16C is a cross section of an adapter with an LED light source and optional camera for the KAVO K4. Note that in this and other embodiments of the invention, not all of the OEM O-rings provided on the stem 1608 of the syringe 1602 are replaced once removed to receive the conversion components. Ferrule 1610 screws into the retainer body 1600, followed by component 1604 including stepped cavities to receive the stepped stem protruding from the syringe system. A radial air flow is produced at 1612.

FIG. 17A is a cross section of an adapter with an LED light source for a CGE syringe. FIG. 17B is a different cross section of the adapter of FIG. 17A illustrating air and water channels. FIG. 17C is a cross section of an adapter with an angled LED light source for a CGE syringe, and FIG. 17D is a cross section of an adapter with an LED light source and optional camera for an ADEC syringe.

Syringes with Existing Light Sources

In addition to adapters that provide light sources to syringes that do not already have light sources, other embodiments of the invention provide adapters that preserve the light from syringes that include lights sources. Two examples will be described in detail as representative, one from Sirona and another from Kayo, with the understanding that other models may be accommodated with appropriate engineering modification apparent to a person of skill in the art.

FIG. 18A is a cross-sectional drawing showing a Sirona syringe 1802 wherein light is brought in via optical conduit 1804. Air and water are delivered via the channels labeled AIR and WATER. To preserve the light, the adapter in this case includes a stem component 1806 with an optical component 1802 that guides the light to a device 1810 enabling the light to exit the body of the adapter at 1812. The disposable tip is indicated at 1800, with other components including the ferrule 1801 being described elsewhere herein.

In FIG. 18A, the component 1810 used for light guiding comprises a 2-piece prism including light guide 1811. As with other embodiments, the light-carrying assembly may include a mirror 1814. As shown in FIG. 18B, the two-piece prism may be replaced with a single-piece light guide 1820. FIG. 18C illustrates the alternate use of an optical fiber 1830. In all embodiments, in the region where the light exits, a light redirection component may be used to aim the light. FIG. 18D, for example, shows such a component 1840, which swivels to direct the light to a desired location. FIG. 18D shows the redirection component 1840 with a multi-prism optical system, whereas FIG. 18E shows the component with a single optical light guide, and FIG. 18F illustrates its use with an optical fiber or conduit.

FIGS. 19A-19E depict the use of an adapter that receives a disposable tip for use in conjunction with a Kayo (Esthetica) model syringe which includes a fiber optic light source. As with FIG. 18, the various diagrams illustrate the use of single and multi-piece prisms, light guides and rotatable redirection components.

The invention claimed is:

1. A method of converting an air/water dental syringe of the type having a syringe body and an autoclavable dental tip and lacking illumination into a converted air/water dental syringe adapted to be used with a disposable dental tip different from the autoclavable dental tip and with illumination capabilities, the method comprising the steps of:
    providing a conversion kit comprising;
        a retainer body including an outer surface, a proximal end with a proximal opening, a distal end with a distal opening and a central passage extending between the openings, the retainer body further including a light bore laterally spaced from the central passage and extending from a base towards the proximal end of the retainer body to a light opening on the outer surface of the retainer body towards the distal opening of the central passage of the retainer body; and
        a self-contained light module including a light-emitting diode (LED), a battery powering the LED, and a switch to turn the LED ON and OFF;
    inserting the self-contained light module into the light bore of the retainer body such the LED is disposed at the light opening, the self-contained light module being removable from the light bore;
    removing the autoclavable dental tip from the syringe body;
    attaching the syringe body to the proximal end of the retainer body, with the inserted light module, through the proximal opening for providing air and water;
    inserting a proximal end of the disposable dental tip into the distal opening of the retainer body;

thereby converting the air/water dental syringe of the type having an autoclavable dental tip and lacking illumination into a converted air/water dental syringe used with a disposable dental tip different from the autoclavable dental tip and with illumination capabilities.

2. The method of claim 1, wherein the conversion kit further includes one or more components within the retainer body having cut-outs, grooves or channels to direct air and water, wherein the disposable dental tip includes a central, water-carrying tube surrounded by air-carrying channels terminating in a distal end, the method further comprising the step of directing air and water from the syringe body to the air-carrying channels and water-carrying tube of the disposable dental tip.

3. The method of claim 1, further comprising the step of emitting light from the LED through the light opening providing illumination generally towards a distal end of the disposable dental tip.

4. The method of claim 1, wherein the light opening of the retainer body is on an outer side surface of the retainer body.

5. The method of claim 1, wherein the switch is in electrical communication with a touch panel on the outer surface of the retainer body used to turn the switch ON and OFF.

6. The method of claim 1, wherein the switch is in electrical communication with a motion detector disposed within the self-contained module, the method further comprising the step of turning on the LED upon the detection of motion and turning off the LED with the absence of motion for a predetermined period of time.

7. The method of claim 1, wherein the conversion kit further includes a lens to direct light from the LED toward the distal end of the disposable dental tip.

8. The method of claim 2, wherein the retainer body or the components therein provide a proximal receptacle to receive a stem on the syringe body.

9. The method of claim 2, wherein the one or more components within the retainer body includes a proximal stem insertable into the syringe body.

10. The method of claim 2, wherein the one or more components within the retainer body includes one or more proximal air- or water-carrying tubes insertable into the syringe body.

11. The method of claim 1, wherein the retainer body includes internal threads for making a threaded connection to the syringe body.

12. The method of claim 1, wherein the retainer body is autoclavable in the absence of the disposable tip.

* * * * *